US009816979B2

(12) United States Patent
Kelso et al.

(10) Patent No.: US 9,816,979 B2
(45) Date of Patent: Nov. 14, 2017

(54) DEVICES AND METHODS FOR FILTERING BLOOD PLASMA

(75) Inventors: David M. Kelso, Wilmette, IL (US); Kunal Sur, Chicago, IL (US); Arman Nabatiyan, Morton Grove, IL (US); Ashley Marie Yanchak Boggiano, Arlington Heights, IL (US); Samuel John Pickerill, Genoa, IL (US); Sujit Jangam, Chicago, IL (US); Shivani Gupta, Evanston, IL (US)

(73) Assignee: Northwestern University, Evanston, IL (US)

( * ) Notice: Subject to any disclaimer, the term of this patent is extended or adjusted under 35 U.S.C. 154(b) by 167 days.

(21) Appl. No.: 13/192,075

(22) Filed: Jul. 27, 2011

(65) Prior Publication Data
US 2012/0024788 A1    Feb. 2, 2012

Related U.S. Application Data

(60) Provisional application No. 61/368,156, filed on Jul. 27, 2010.

(51) Int. Cl.
G01N 33/49    (2006.01)
B01L 3/00    (2006.01)
B01D 61/00    (2006.01)

(52) U.S. Cl.
CPC .......... *G01N 33/491* (2013.01); *B01L 3/5023* (2013.01); *B01L 2200/026* (2013.01); *B01L 2300/0681* (2013.01)

(58) Field of Classification Search
CPC ............. B01L 3/5023; B01L 2200/026; B01L 2300/0681; C12Q 1/00; G01N 33/491; G01N 33/558

USPC ....... 210/645, 650, 651, 654, 483, 488, 489, 210/490, 491, 500.21, 500.41, 500.26, 210/501, 502.1, 503–508; 422/401, 412, 422/420–429, 73, 502, 507, 513, 534, 422/535, 547, 560
See application file for complete search history.

(56) References Cited

U.S. PATENT DOCUMENTS

| 4,256,693 | A |   | 3/1981 | Kondo et al. |
|---|---|---|---|---|
| 4,477,575 | A |   | 10/1984 | Vogel et al. |
| 4,753,776 | A |   | 6/1988 | Hillman et al. |
| 4,816,224 | A |   | 3/1989 | Vogel et al. |
| 5,186,843 | A |   | 2/1993 | Baumgardner et al. |
| 5,240,862 | A | * | 8/1993 | Koenhen ............... B01L 3/5023 210/500.24 |
| 5,423,989 | A | * | 6/1995 | Allen et al. .................... 210/650 |
| 5,589,399 | A | * | 12/1996 | Allen et al. .................... 436/169 |
| 6,036,659 | A | * | 3/2000 | Ray et al. ....................... 600/573 |
| 6,197,598 | B1 | * | 3/2001 | Schrier et al. ................ 436/518 |

(Continued)

OTHER PUBLICATIONS

Baskurt et al, "Blood rheology and hemodynamics", Seminars in Thrombosis and Hemostasis, vol. 29, No. 5, pp. 435-450 (2003).

(Continued)

*Primary Examiner* — John Kim
(74) *Attorney, Agent, or Firm* — Jacqueline F. Mahoney; Judy M. Mohr; McDermott Will & Emery LLP

(57) ABSTRACT

The present invention provides systems, devices, kits, and methods for separating blood plasma from whole blood. In particular, the present invention provides systems, devices, and methods for separating a fixed volume of blood plasma from whole blood with minimal energy input.

17 Claims, 32 Drawing Sheets

(56) References Cited

U.S. PATENT DOCUMENTS

| | | | |
|---|---|---|---|
| 7,228,973 | B2 | 6/2007 | Simon |
| 2001/0005488 | A1 | 6/2001 | Hirao et al. |
| 2003/0186457 | A1 | 10/2003 | Iwaki et al. |
| 2003/0206828 | A1 | 11/2003 | Bell |
| 2007/0269893 | A1 | 11/2007 | Blankenstein et al. |
| 2008/0153096 | A1* | 6/2008 | Witty et al. ............ 435/6 |
| 2009/0246782 | A1 | 10/2009 | Kelso et al. |
| 2010/0092979 | A1 | 4/2010 | Kelso et al. |
| 2011/0076697 | A1* | 3/2011 | Ruvinsky et al. ........ 435/7.25 |

OTHER PUBLICATIONS

Benson, "MCAT Review Problem #9", Emory University Online, 2 pgs. (1999) Abstract only.

Blattert et al., "Separation of blood in microchannel bends", Proceedings of the 26th Annual International Conference of the IEEE EMBS, pp. 2627-2630 (2004).

Brenner et al., "Continuous centrifugal separation of whole blood on a disk", 8th International Conference on Miniaturized Systems for Chemistry and Life Sciences, vol. 296, pp. 566-568 (2004).

Chien, "Red cell deformability and its relevance to blood flow", Annual Review of Physiology, vol. 49, pp. 177-192 (1987).

Dineva et al., "Sample preparation: a challenge in the development of point-of-care nucleic acid-based assays for resource-limited settings", Analyst, vol. 132, pp. 1193-1199 (2007).

Haeberle et al., "Centrifugal extraction of plasma from whole blood on a rotating disk", Lab on a Chip, vol. 6, No. 6, pp. 776-781 (2006).

Huang et al., "Thermodynamically modulated partially double-stranded linear DNA probe design for homogenous real-time PCR", Nuc. Acids Res., vol. 35, No. 16, pp. e101 (2007).

Kang et al., "Novel particle separation using spiral channel and centrifugal force for plasma preparation from whole blood", 8th International Conference on Miniaturized Systems for Chemistry and Life Sciences, vol. 296, pp. 614-616 (2004).

Loewen et al., "Development of a nonwoven filler for separation of serum from whole blood for medical diagnostic applications", Tappi Journal, vol. 79, No. 12, pp. 183-184 (1996).

Luo et al., "Detection of human immunodeficiency virus type 1 DNA in dried blood spots by a duplex real-time PCR assay", J. Clin. Microbiol., vol. 43, No. 4, pp. 1851-1857 (2005).

Madou et al., "Design and fabrication of CD-like microfluidic platform for diagnostics: microfluidic functions", Biomedical Microdevices, vol. 3, No. 3, pp. 245-254 (2001).

Mylonakis et al., "Plasma viral load testing in the management of HIV infection", Am. Fam. Physician, vol. 63, No. 3, pp. 483-490 (2001).

Suzuki and Ho, "A magnetic force driven chaotic micro-mixer", 15th IEEE International Conference on Micro Electro Mechanical Systems, pp. 40-43 (2002).

Toner et al., "Blood-on-a-chip", Annual Review of Biomedical Engineering, vol. 7, pp. 77-103 (2005).

International Search Report from related PCT Patent Application No. PCT/US2011/045541 dated Mar. 13, 2012, application now published as International Publication No. WO 2012/015926 dated Feb. 2, 2012.

\* cited by examiner

DEVICES AND METHODS FOR FILTERING BLOOD PLASMA

This application claims priority to U.S. Provisional Patent Application Ser. No. 61/368,156, filed Jul. 27, 2010, which is herein incorporated by reference in its entirety.

FIELD OF THE INVENTION

The present invention provides systems, devices, kits, and methods for separating blood plasma from whole blood. In particular, the present invention provides systems, devices, and methods for separating a volume (e.g., fixed volume) of blood plasma from whole blood with minimal energy input.

BACKGROUND

Several up-stream processes are required before a complex biological fluid can be analyzed for analytes. For example, to perform HIV viral load detection, the separation of plasma from blood is the first up-stream step since hemoglobin and blood cells interfere with the subsequent amplification and detection of viral RNA. The separation of plasma is also a critical upstream process for the detection and diagnosis of infectious diseases. For example, the detection of HIV in adults using HIV-specific antibodies or the detection of HIV in infants by using an HIV core p24 protein require the separation of plasma from whole blood.

In a laboratory setting, the separation of plasma from whole blood is carried out by centrifugation of blood for 20 minutes at 3000 g. In doing so, the solid components of blood settle down in the sediment and the supernatant liquid consists of plasma. This protocol usually requires a trained technician to manually pipette out the supernatant for further analysis. While large scale automated sample preparation systems can eliminate the manual step, these instruments are expensive instrumentation, making them unsuitable for resource limited or point-of-care testing.

Methods have been designed to integrate the centrifugal blood separation with further downstream steps through a micro-fluidic platform (Brenner et al. Special Publicatlon-Royal Society of Chemistry 2004, 296:566-568., Haeberle et al. Lab on a Chip 2006, 6:776-781., Kang et al. Special Publicatlon-Royal Society of Chemistry 2004, 296:614-616., Madou et al. Biomedical Microdevices 2001, 3:245-254., Toner & Irimia. Annual Review of Biomedical Engineering 2005, 7:77-103., Luo et al. J Clin Microbio/2005, 43:1851-1857., herein incorporated by reference in its entirety). However, these methods work with an extremely limited volume of whole blood, require the use of an instrument to create the centrifugal force, are prone to clogging, and/or achieve only limited purity. The use of synthetic membranes to separate blood from plasma avoids some of the problems presented by centrifugation and microfluidics systems; however, devices are complex due to the need for multiple filter layers (Vogel et al. Boehringer Mannheim GmbH; 1984., Vogel et al. Boehringer Mannheim GmbH; 1989., herein incorporated by reference in their entireties), are inherently fragile and difficult to use do to the membrane materials used (e.g., glass fiber), comprise materials which interfere with assays (Baumgardner & Loewen. Ahlstrom Filtration, Inc.; 1993., Loewen & Baumgardner. Tappi Journal 1996, 79:183-184., herein incorporated by reference in their entireties), and contain materials which retard the flow of blood into the filters (Suzuki & Ho: A magnetic force driven chaotic micro-mixer. pp. 40-43; 2002: 40-43., herein incorporated by reference in its entirety).

SUMMARY OF THE INVENTION

In some embodiments, the present invention provides a method of filtering blood plasma comprising: (a) providing: (i) a filter module, wherein the filter module comprises a filter configured to allow passage of blood plasma but not other blood components; (ii) a plasma collection module, wherein the plasma collection module comprises a collection membrane configured to draw blood plasma into the plasma collection module by capillary action; and (iii) a blood sample; (b) applying the blood sample to the filter of the filter module; (c) placing the collection membrane of the plasma collection module into direct contact with the filter of the filter module; and (d) drawing the blood plasma through the filter into the plasma collection module. In some embodiments, the drawing is passive. In some embodiments, the drawing does not require electrophoresis, centrifugation, or greater than atmospheric pressure. In some embodiments, the filter module accommodates a fixed volume of blood sample. In some embodiments, the plasma collection module accommodates a fixed volume of plasma. In some embodiments, the fixed volume of the plasma collection module is smaller than the fixed volume of the filter module. In some embodiments, the fixed volume of the plasma collection module is independent of the volume of the blood sample. In some embodiments, the fixed volume of the plasma collection module is independent of the hematocrit of the blood sample. In some embodiments, the filter comprises a VIVID GF membrane. In some embodiments, the collection membrane comprises an AHLSTROM 142 fiber collection pad. In some embodiments, the collection membrane comprises a PALL A/D fiber collection pad. In some embodiments, the method further comprises (e) storing plasma in the plasma collection module.

In some embodiments, the present invention provides a device for separating plasma from whole blood comprising: (a) a filter module, wherein the filter module comprises a filter configured to allow passage of blood plasma but not other blood components; and (b) a plasma collection module, wherein the plasma collection module comprises a collection membrane configured to draw blood plasma into the plasma collection module by capillary action. In some embodiments, the filter module accommodates a fixed volume of whole blood. In some embodiments, the plasma collection module accommodates a fixed volume of plasma. In some embodiments, the fixed volume of the plasma collection module is smaller than the fixed volume of the filter module. In some embodiments, the filter comprises a VIVID GF or VIVID GR membrane. In some embodiments, the collection membrane comprises an AHLSTROM 142, PALL ACCUWIK, or PALL A/D fiber collection pad. In some embodiments, the device comprises PMPs in the collection module. In some embodiments, the device comprises assay reagents in the collection module.

Additional embodiments are described herein.

DEFINITIONS

Figure 1:
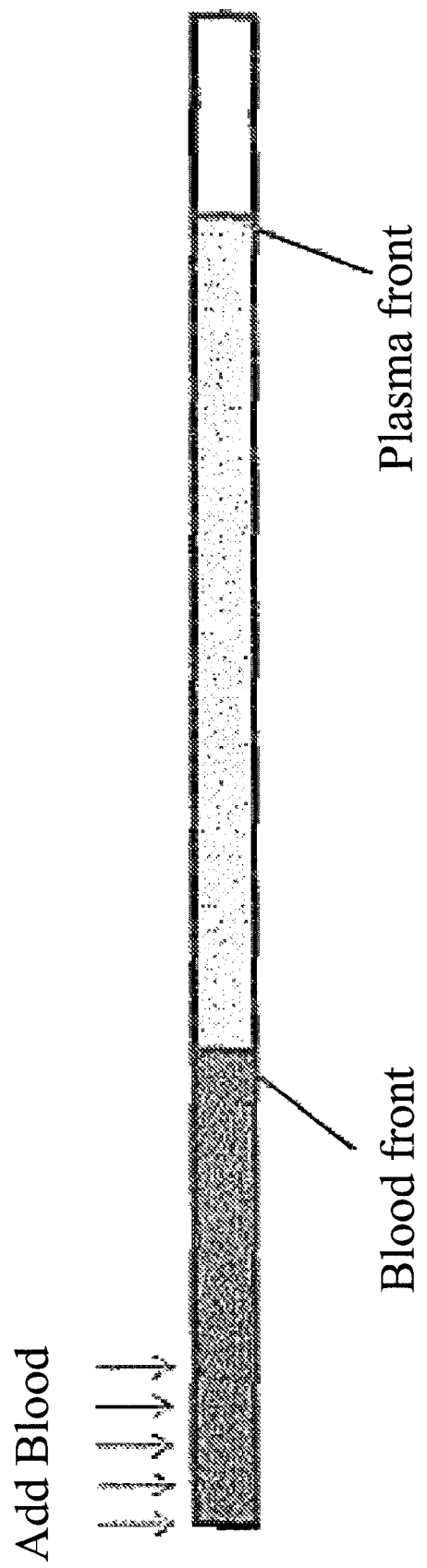
FIG. 1 shows side view of membrane showing the point of blood addition on the membrane, the blood front and the plasma front on the membrane.

To facilitate an understanding of the present invention, a number of terms and phrases are defined below:

As used herein, the term "subject" refers to organisms to be treated by the methods of the present invention. Such organisms preferably include, but are not limited to, mammals (e.g., murines, simians, equines, bovines, porcines, canines, felines, primates, etc.), and most preferably humans. In the context of the invention, the term "subject" typically refers to one who has had provided a sample, or had a sample taken (e.g., tissue sample, fluid sample (e.g., blood sample)). The term "patient" is commonly used when referring to a human subject.

The term "diagnosed," as used herein, refers to the recognition of a disease by its signs and symptoms (e.g., resistance to conventional therapies), or genetic analysis, pathological analysis, histological analysis, and the like.

As used herein the term, "in vitro" refers to an artificial environment and to processes or reactions that occur within an artificial environment. In vitro environments include, but are not limited to, test tubes. The term "in vivo" refers to the natural environment (e.g., an animal or a cell) and to processes or reaction that occur within a natural environment.

As used herein, the term "sample" as used herein is used in its broadest sense. A sample may comprise a cell, tissue, or fluids (e.g., blood, plasma, etc.), material isolated from a cell, genomic DNA (in solution or bound to a solid support such as for Southern blot analysis), RNA (in solution or bound to a solid support such as for Northern blot analysis), cDNA (in solution or bound to a solid support) and the like.

As used herein, the terms "to isolate" or "isolated" refer to a sample that is identified and separated from at least one component or contaminant with which it is ordinarily associated in its natural source. An isolated sample is such present in a form or setting that is different from that in which it is found in nature. In contrast, a non-isolated sample is found in the state they exist in nature.

As used herein, the terms "purified" or "to purify" refer to the removal of components (e.g., contaminants, undesired components) from a sample. As used herein, the term "substantially purified" refers to molecules that are at least 60% free, preferably 75% free, and most preferably 90%, 95%, 99%, or more, free from other components with which they usually associated.

DETAILED DESCRIPTION OF THE INVENTION

The present invention provides systems, devices, kits, and methods for separating blood plasma from whole blood. In particular, the present invention provides systems, devices, and methods for separating a volume (e.g., fixed volume) of blood plasma from whole blood with minimal energy input. In some embodiments, the present invention provides systems and devices for separating blood plasma from whole blood. In some embodiments, devices separate blood plasma from other blood components (e.g., blood cells). In some embodiments, devices purify blood plasma. In some embodiments, devices isolate blood plasma. In some embodiments, devices concentrate blood plasma. In some embodiments, devices effectively separate and concentrate a fixed volume of plasma from whole blood. In some embodiments, the present invention separates, isolates, purifies, and/or concentrates blood plasma from whole blood without additional energy input (e.g., no requirement for heating, centrifuging, electricity, etc.). In some embodiments, the present invention provides a filter element, and a collection element. In some embodiments, whole blood (e.g., unfiltered) is added to a filter element, and the blood is drawn (e.g., by capillary action, by gravity, etc.) through the filter element toward the collection element.

Figure 24:
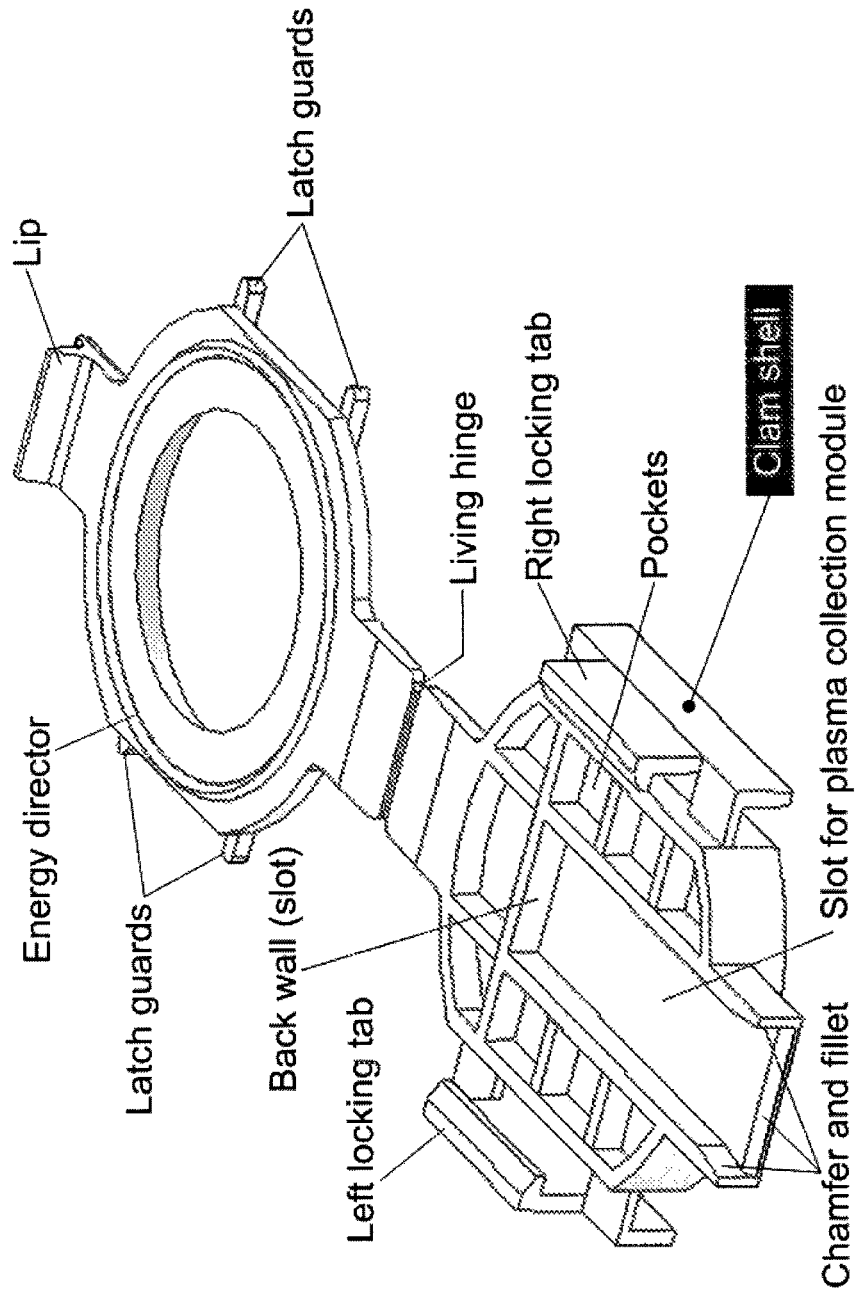
FIG. 24 shows a schematic of a clam shell disposable (single-use) plastic component, part of the filter element. The clam shell integrates a separation filter into itself, and interface with an external plasma collection element, which contains the collection membrane.
Figure 25:
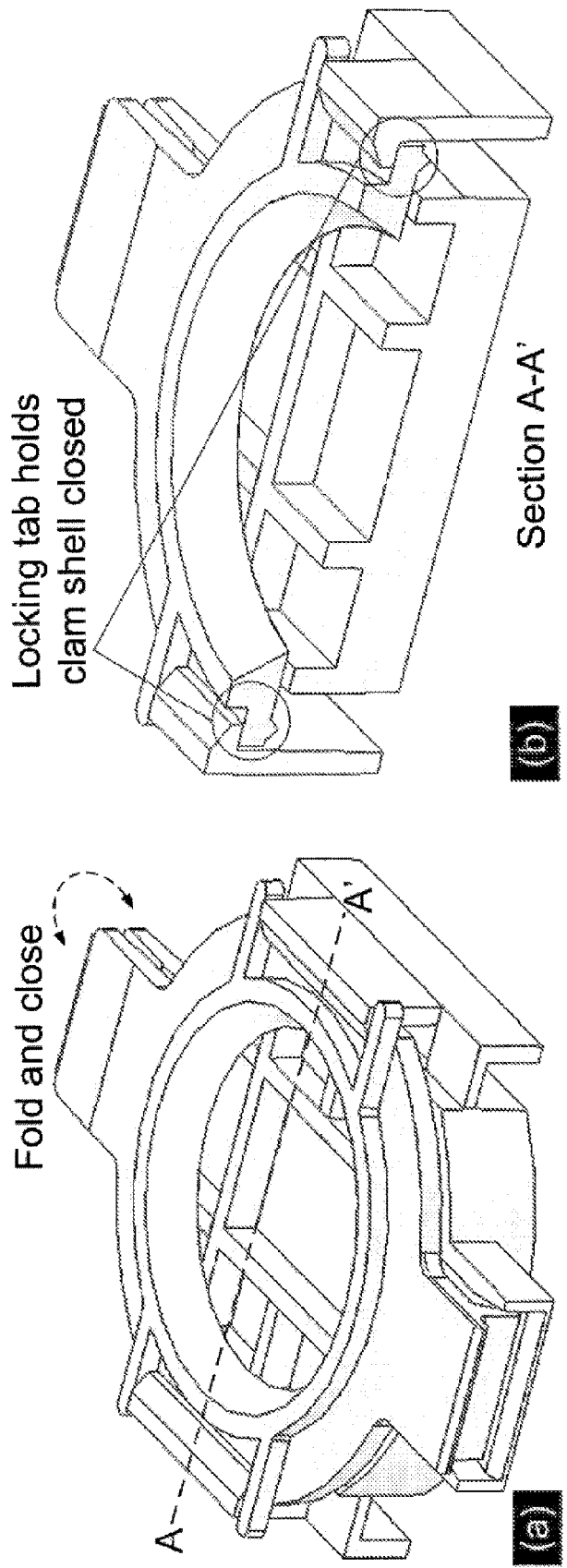
FIG. 25 shows (a) the top-half of a clam shell is folded over and closed. The left and right latching tabs lock and hold the clam shell closed, as shown in the section-view schematic in (b).
Figure 26:
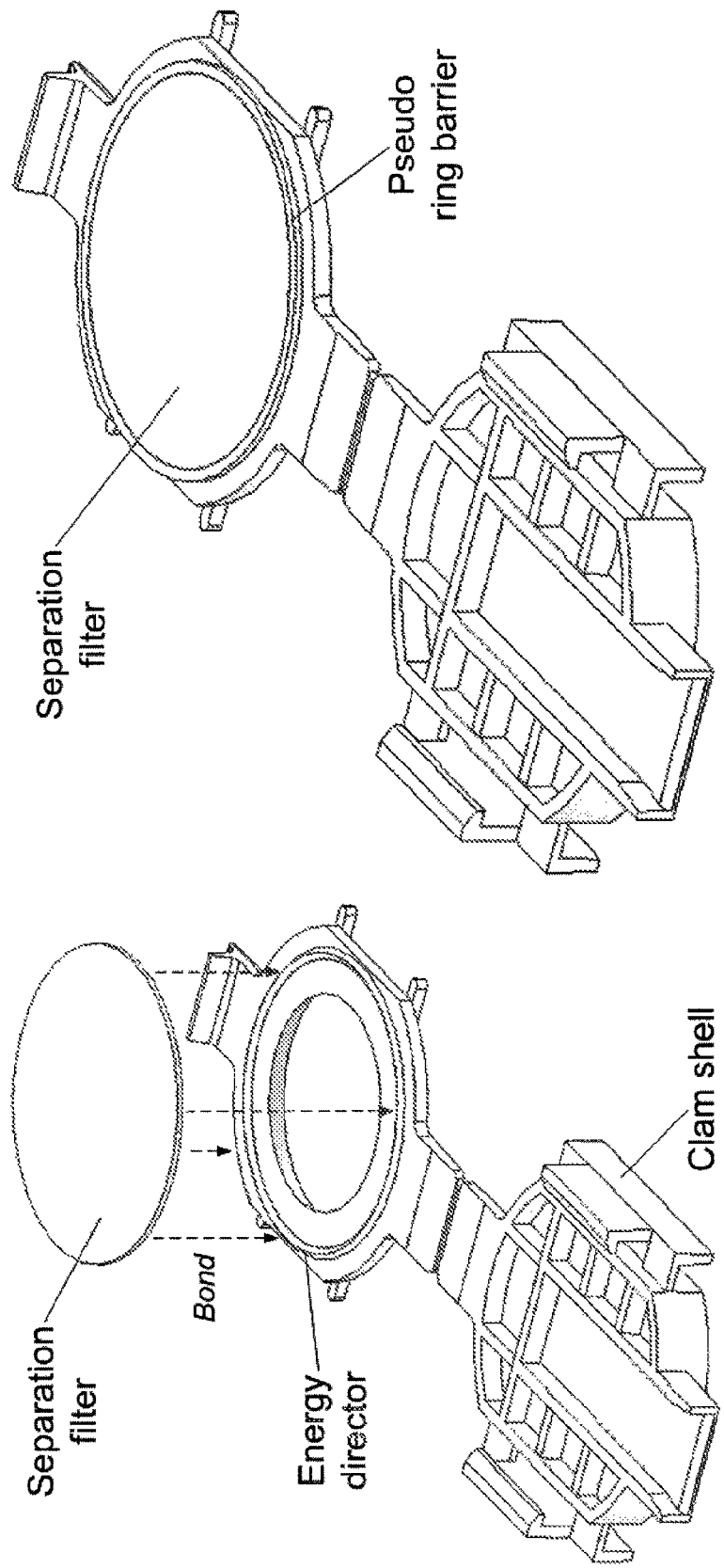
FIG. 26 shows (left) a schematic of the clam shell plastic part. A separation filter is aligned and bonded to the clam shell, here, via the energy director using ultrasonic welding; and (right) a schematic of the integrated clam shell and separation filter. The energy director plastic melts and flows into the separation filter, creating a pseudo ring barrier.
Figure 27:
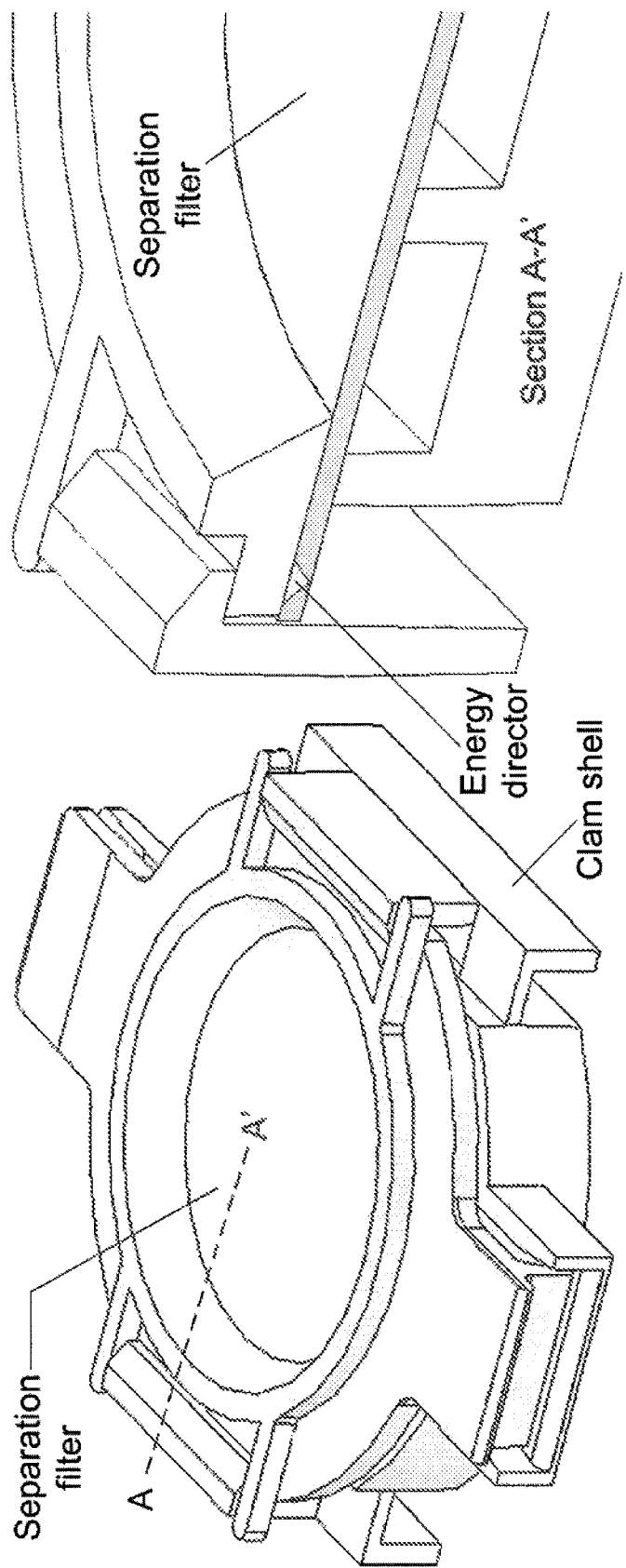
FIG. 27 shows (left) a schematic of a closed and locked clam shell, which has a separation filter bonded to it (e.g., via ultrasonic welding using an energy director); and (Right) a section-view of the left schematic showing that the separation filter is bonded such that when the clam shell is closed, it is flush with the bottom-half of the clam shell.

In some embodiments, the present invention provides a filter element. In some embodiments, one or more blood components (e.g., cellular components) move more slowly through the filter element than blood plasma. In some embodiments, blood components other than plasma (e.g., cellular components) move more slowly through the filter element than blood plasma. In some embodiments, one or more blood components (e.g., cellular components) are unable to move through the filter element. In some embodiments, blood components other than plasma (e.g., cellular components) are unable to move through the filter element. In some embodiments, blood plasma rapidly (e.g., more rapidly than other blood components) advances through the filter element toward and/or into the collection element. In some embodiments, the filter element comprises a filter, membrane, matrix, and/or pad capable of separating blood plasma from other blood components based on capillarity. Although the present invention is not limited to any particular mechanism of action and an understanding of the mechanism of action is not necessary to practice the present invention, the movement of a liquid through a material by capillary action is governed by the equation:

$$d=(2\gamma \cos \theta)/(\rho g r)$$

wherein $\gamma$ is the liquid-air surface tension (energy/area), $\theta$ is the contact angle, $\rho$ is the density of liquid (mass/volume), g is acceleration due to gravity (length/time$^2$), and r is radius path through the material (length). Therefore, different liquids move through a material at different rates based on the liquid-air surface tension and the density for the liquids. In some embodiments, plasma moves more quickly through a material (e.g., filter element) than other blood components (e.g., cellular components). In some embodiments, the present invention separates blood plasma from other whole blood components based on differences in the rate of capillary movement through a filter material. In some embodiments, a filter element comprises a filter and/or membrane configured to allow passage of blood plasma and other whole blood components at different rates. In some embodiments, a filter element comprises a plasma separation membrane. In some embodiments, a filter element comprises a VIVID Plasma Separation Membrane. In some embodiments, a filter element comprises a VIVID GF Plasma Separation Membrane. In some embodiments, a filter element is configured to separate a defined volume of whole blood (e.g., 15 µL, 25 µL, 50 µL, 75 µL, 100 µL, 125 µL, 150 µL, 200 µL, 300 µL, 400 µL, 500 µL, 750 µL, 1 mL, 2 mL, 3 mL, etc.). In some embodiments, filter element comprises a membrane of any suitable size. In some embodiments, filter element comprises a membrane of any suitable diameter (e.g., 5 mm . . . 8 mm . . . 10 mm . . . 12 mm . . . 15 mm . . . 18 mm . . . 20 mm . . . 25 mm . . . 30 mm . . . 40 mm . . . 50 mm, etc.). The present invention is not limited by the materials used in the filter element, and any material understood by one in the field to provide suitable filtration qualities may find use with the present invention. In some embodiments, a filter element is disposable. In some embodiments, a filter element is reusable. In some embodiments, a filter comprises a molded clam shell (e.g., disposable molded clam shell) (SEE FIGS. 24-25). In some embodiments, a filter element comprises a shell (e.g., single-use shell) and a separation filter (SEE FIGS. 26-27). In some embodiments, a clam shell component is injection molded (e.g., from a molded plastic resin). In some embodiments, a filter element comprises a clam shell component integrated with a separation filter. The present invention is not limited by the materials or configuration used in the filter element, and any material understood by one in the field to provide suitable filtration qualities may find use with the present invention.

In some embodiments, the present invention provides a collection element. In some embodiments, a collection element comprises a substrate, pad, matrix, material, and/or filter. In some embodiments, a collection element is configured to collect a fixed volume of plasma from a whole blood sample (e.g., 10 µL, 20 µL, 30 µL, 40 µL, 50 µL, 60 µL, 70 µL, 80 µL, 90 µL, 100 µL, 200 µL, 300 µL, 400 µL, 500 µL, 1 mL, etc.). In some embodiments, a collection element comprises a plasma separation membrane, collection pad, collection matrix, etc. In some embodiments, a collection element comprises one or more of glass fiber, polyester, nitrocellulose and/or cellulose. In some embodiments, a collection element comprises one or more materials selected from WHATMAN Fusion 5 (Whatman Diagnostic Catalogue 2010, page 8; herein incorporated by reference in its entirety), PALL ACCUWICK, PALL A/D, AHLSTROM 111 (Ahlstrom Laboratory Products Catalog (2009), page 15; herein incorporated by reference in its entirety), AHLSTROM 151 (Ahlstrom Laboratory Products Catalog (2009), page 15; herein incorporated by reference in its entirety), and/or AHLSTROM 142 (Ahlstrom Laboratory Products Catalog (2009), page 15; herein incorporated by reference in its entirety) membranes, and/or any other suitable membranes, pads, or matrix materials known to those of skill in the art. In some embodiments, a collection element comprises an AHLSTROM 142 collection membrane. In some embodiments, filter element comprises a membrane of any suitable diameter (e.g., 2 mm . . . 4 mm . . . 6 mm . . . 8 mm . . . 10 mm . . . 12 mm . . . 15 mm . . . 20 mm . . . 30 mm . . . 40 mm . . . 50 mm, etc.). In some embodiments, a collection element comprises a substrate test strip, diagnostic double-sided adhesive, and collection membrane. In some embodiments, a collection element comprises a collection membrane. In some embodiments, a collection element comprises a diagnostic double-sided adhesive. In some embodiments, a collection element comprises a substrate test strip. In some embodiments, a collection element comprises a substrate test strip, diagnostic double-sided adhesive, and collection membrane. The present invention is not limited by the materials used in the collection element or its configuration, and any material or configuration understood by one in the field to provide suitable collection qualities may find use with the present invention.

In some embodiments, a filter element and collection element comprise a single unit. In some embodiments, a filter element and collection element comprise separate collection and filter modules. In some embodiments, a separation module and filter module are operable connected and/or connectable. In some embodiments, a filter module comprises a filter element. In some embodiments, a filter element (e.g., membrane) in a filter module is replaceable and the filter module is reusable with a new filter element (e.g., membrane). In some embodiments, a collection module comprises a collection element. In some embodiments, a collection element (e.g., membrane) in a collection module is replaceable and the collection module is reusable with a new collection element (e.g., membrane).

In some embodiments, the present invention provides a matrix within a collection module to collect blood (e.g., from a finger-stick, from a vein, etc.). In some embodiments, the present invention provides a matrix to collect blood from a finger-stick. In some embodiments, the present invention separates cells from plasma when whole blood is added. In some embodiments, the amount of blood required is minimized by maximizing the efficiency of plasma separation.

Figure 7:
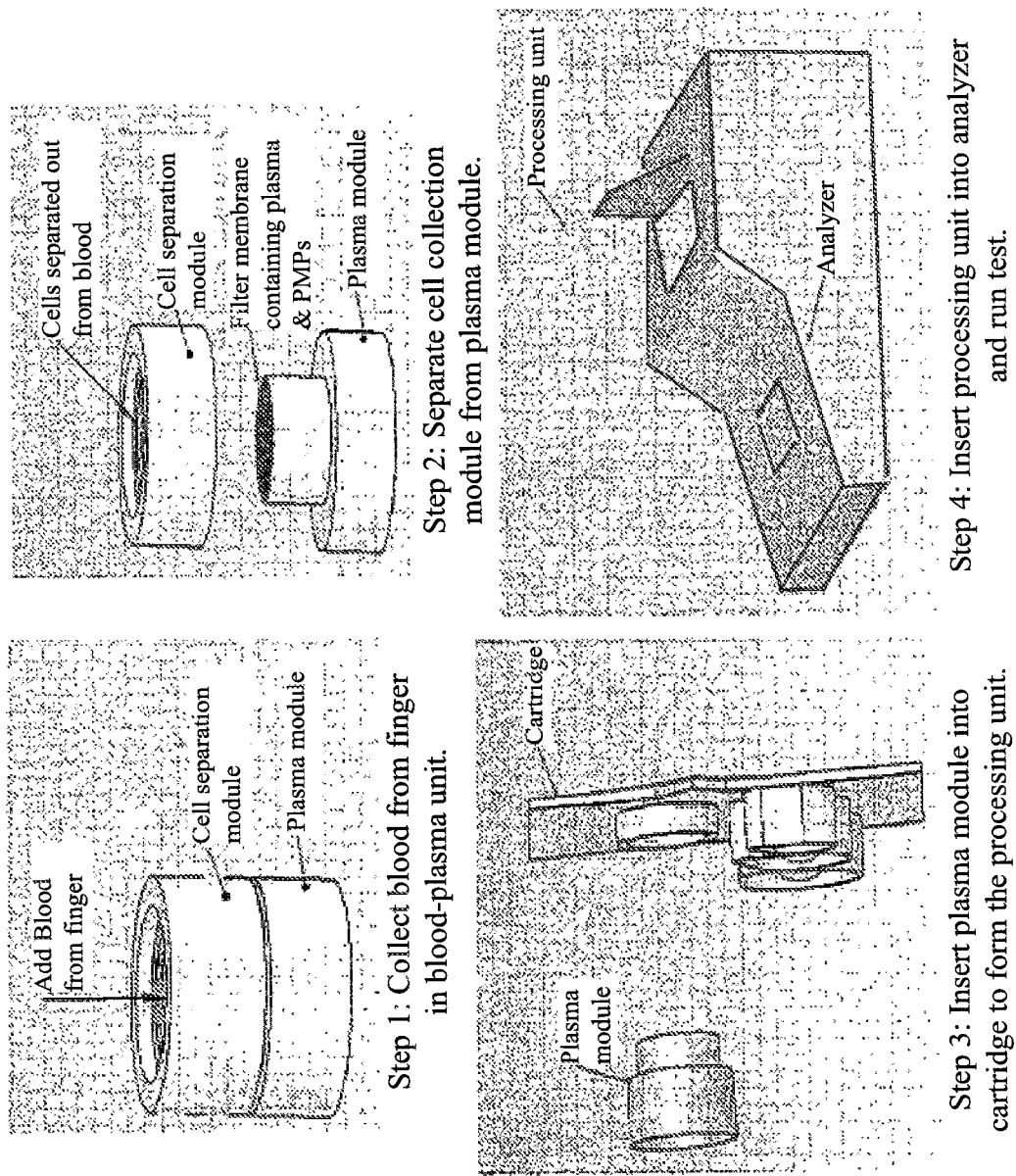
FIG. 7 shows an exemplary blood plasma unit design. The blood plasma unit has two parts, a cell separation module and a plasma module. After separation, the plasma module is removed and transferred to the cartridge for processing in the system analyzer.

In some embodiments, devices of the present invention provide separation of whole blood components (e.g., blood cells) from plasma. In some embodiments, the separated plasma and cellular components can each be used for subsequent applications (e.g., testing). For example, cellular blood components are separated from plasma to monitor CD4 count, and the plasma component is used for measuring viral load. By utilizing both the cellular and plasma components, devices of the present invention provide samples for multiple different assays (SEE FIG. 7).

In some embodiments, systems, devices, and methods provide timed separation of plasma components from cellular components in whole blood. In some embodiments, separation of plasma from other blood components is complete in less than 1 hour (e.g., 45 minutes . . . 30 minutes . . . 20 minutes . . . 15 minutes . . . 10 minutes . . . 8 minutes . . . 6 minutes . . . 5 minutes . . . 4 minutes . . . 3 minutes . . . 2 minutes . . . 1 minutes . . . 30 seconds).

In some embodiments, systems, devices, and methods collect a fixed amount of plasma. In some embodiments, systems, devices, and methods collect a fixed amount of plasma on a membrane, filter, and/or pad (e.g., ALLSTOM 142). In some embodiments, the present invention collects a fixed volume of plasma and therefore provides a measuring device. In some embodiments, devices of the present invention collect a fixed volume of plasma, independent of the volume of blood added. In some embodiments, devices of the present invention collect a fixed volume of plasma, independent of the hematocrit of the blood added. In some embodiments, systems, devices, and methods of the present invention collect a fixed volume of plasma from a whole blood sample (e.g., 10 µL, 20 µL, 30 µL, 40 µL, 50 µL, 60 µL, 70 µL, 80 µL, 90 µL, 100 µL, 200 µL, 300 µL, 400 µL, 500 µL, 1 mL, etc.). In some embodiments, systems, devices, and methods of the present invention collect approximately 50 µL of blood plasma. In some embodiments, devices of the present invention provide collection of a volume of plasma selected to provide a desired viral load in the sample (e.g., a volume of 50 µL provides an assay sensitivity of 600 HIV copies/mL of blood for HIV viral load detection by RT-PCR).

In some embodiments, devices, systems, and methods of the present invention operate passively, not requiring any active pumping, centrifugation, electrophoresis, and/or electricity to operate. In some embodiments, passive separation is achieved via capillary action and/or gravity. In some embodiments, devices, system, and methods of the present invention provide plasma separation in non-laboratory, remote locations (e.g., in the field), and/or point-of-care location In some embodiments, a collection element (e.g., membrane) is smaller than the separation element (e.g., membrane). In some embodiments, a device and/or system in which the collection element (e.g., membrane) is smaller than the separation element (e.g., membrane) serves to concentrate plasma into a small volume. In some embodiments, concentration of blood plasma into a small collection element is useful for downstream analytical steps that require increased sensitivity (e.g., an immunoassay, or for improved nucleic acid capture onto a paramagnetic particle).

In some embodiments, a device of the present invention, a collection element, and/or a collection module provide and/or serve as a blood plasma storage element. In some embodiments, the present invention provides a blood plasma storage element. In some embodiments, blood plasma is stored in the collection element (e.g., collection matrix). In some embodiments, plasma is transported while contained within the collection element. In some embodiments, a filter element containing filtered blood components is discarded prior to storage and/or transportation of blood plasma.

In some embodiments, a device of the present invention, a collection element, and/or a collection module is integrated with downstream processes (e.g., a cartridge or other device for HIV viral RNA extraction, purification and amplification; a lateral flow system for the detection of HIV antibodies or p24 protein; etc.). In some embodiments, a device or system of the present invention comprises downstream modules for analysis or further manipulation of separated blood plasma. In some embodiments, a collection element allows extraction of collected plasma directly into buffer for further analysis and/or manipulation. For viral load applications, the plasma collection membrane allows for the extraction of the viral RNA present in the plasma directly into buffer (e.g., Ambion lysis/binding buffer (Applied Biosystem)) for further down-stream processing. In some embodiments, direct extraction from the collection element eliminates handling steps associated with other protocols which can result in loss, contamination, or damage of the sample. For lateral flow applications, the plasma collection membrane allows for the extraction of proteins (e.g., HIV-specific antibodies, p24 core proteins, etc.) for further downstream processing. In some embodiments, assay reagents can be stored (e.g., dried or lyophilized) in the plasma collection module. In some embodiments, a collection element provides a matrix for storage (e.g., long term storage) of paramagnetic particles (PMPs). In some embodiments, PMPs which are used for capture nucleic acids (e.g., viral RNA) and subsequent processing. In some embodiments, a collection element allows the PMPs to be extracted out of the membrane using a magnetic force (e.g., generated by a permanent magnet or an electro-magnet), eliminating the need for solution agitation and centrifugation, steps typically associated with samples collected in filter membranes for PCR applications.

In some embodiments, kits are provided comprising one or more or all of the components necessary, sufficient, or useful for making or using any of the devices described herein. In some embodiments, kits comprise control reagents, instructions (e.g., software), data analysis devices, or any other desired components.

EXPERIMENTAL

Example 1

Method of Separation

Lateral-Flow Separation.

Figure 2:
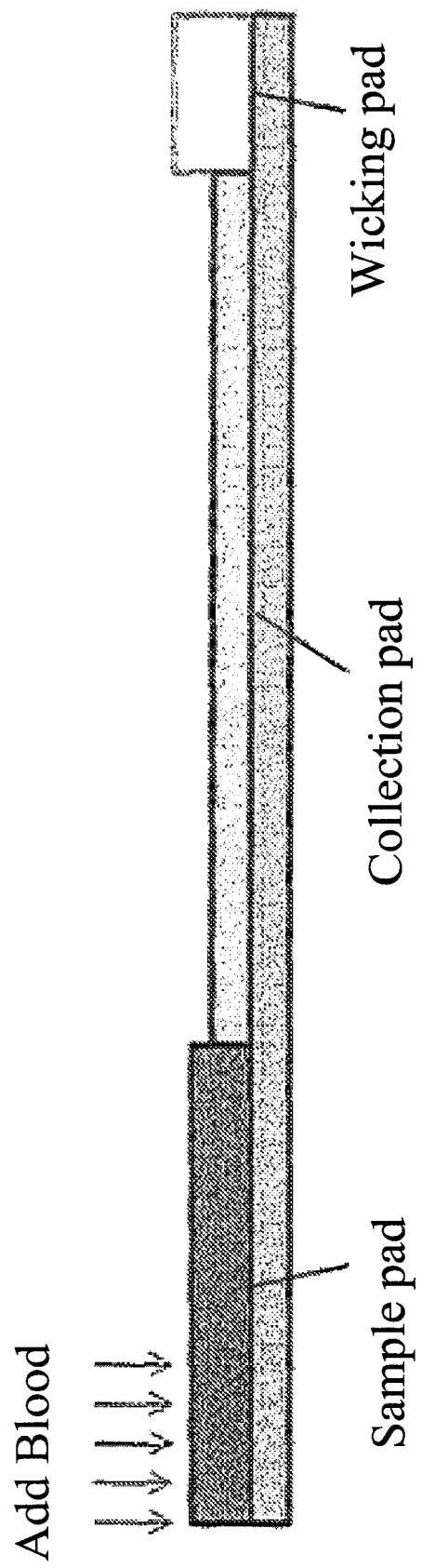
FIG. 2 shows a lateral flow configuration showing the sample pad that separated the blood cell from plasma, collection pad that collects a fixed volume of plasma, and a wicking pad to collect the extra plasma.

Three different lateral flow membranes, namely Pall Cytosep 1662, Watman Fusion 5, Whatman MF1 were tested for plasma separation in a lateral flow configuration (SEE FIG. 1). Membranes were selected based on manufacturer's recommendations, ability to separate plasma from 100-200 µL of whole blood without clogging, pore size, and filter capacity. As the blood flows through the membrane, the plasma front moves faster than the blood front (SEE FIG. 1). The blood section can be eliminated by cutting the red section of the membrane. The volume of plasma collected was determined by weighing the filter paper before and after collection and assuming the density of plasma to be 1025 Kg/m$^3$ (Benson K: MCAT review. Emory University 1999: 141-199., herein incorporated by reference in its entirety). Using a blood sample collected by venipuncture with a hematocrit of 50%, the highest plasma recovery was observed with the Cytosep membrane at 75%. While these recovery percentages could be improved further by the addition of a collection pad with a higher capillary number (SEE FIG. 2), this method exhibited the following limitations: (1) the flow rate was slow making the process time consuming, (2) the position of the blood front varied with hematocrit, volume of blood added, and other rheological properties of the blood, requiring the user to manually locate the blood front and cut the membrane to separate the plasma from the whole blood (3) collecting a fixed volume of plasma would also require punching out a fixed length of plasma containing membrane, which depends on the capacity of the membrane.

The need for the punching step was eliminated by using an alternative configuration (SEE FIG. 2), where the blood is collected in a sample pad which prevents the blood cells from flowing into the collection pad. The collection pad is sized to collect a fixed volume of plasma. The extra plasma flows into the wicking pad, which acts like a reservoir. However, experiments performed during development of embodiments of the present invention demonstrated that the red blood cell front does not stop completely, and none of the above mentioned membranes completely prevent the cells from leaking out into the collection pad. To eliminate this problem, the sample pad was made large enough to accommodate for the variability of blood volume associated with collection from a finger stick. However, this reduces the efficiency of plasma collection. Another solution to the problem was to add a precise amount of blood to the sample pad. This can be achieved by first collecting the blood into a capillary tube with an indicator for blood volume and then adding it to the sample pad. However, this method adds an extra step to the process.

Vertical-Flow Separation.

Figure 3:
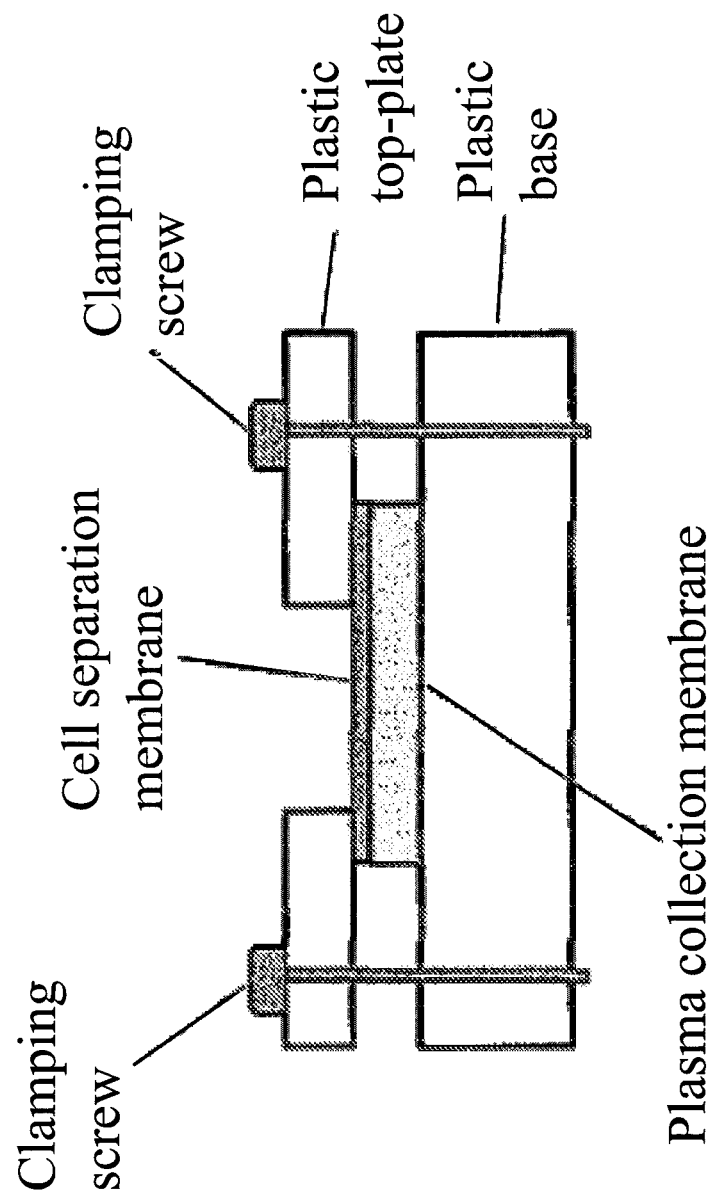
FIG. 3 shows vertical flow set-up: the cell separation and the plasma collection membrane are clamped between a plastic top plate and a base plate.

Plasma separation was carried out in a vertical-flow configuration (SEE FIG. 3). Red and white blood cells are captured by the separation membrane due to its small pore size whereas the plasma component of blood flows through to the collection membrane. The plasma flow rate, Q is directly proportional to the cross-sectional area of flow and inversely proportional to the length of flow. Due to the large cross-sectional area and small length of flow compared to lateral flow, separation of plasma from cells is faster in vertical flow than in lateral flow.

Example 2

Membrane

Membranes were selected based on several criteria, e.g., efficiency of plasma extraction from whole blood, and ease of RNA extraction from the membrane in the lysis/binding buffer (Applied Biosystem, Carlsbad, Calif.) containing ethanol and guanidinium thiocyanate (GuSCN). Experiments were performed during development of embodiments of the present invention to determine the efficiency of plasma separation from whole blood, and sample collection, for selected membranes (SEE FIG. 3). PALLCytosep 1662, Whatman VF1 and PALL VIVID GR were tested for plasma separation and Ahlstrom 111, Ahlstrom 142, Whatman MF1 and PALL ACCUWIK Ultra were tested for sample collection.

Plasma Separation.

The separation membrane was sized for 100 µL of blood using the manufacturer's recommendations. The collection membrane was sized for 50 µL of plasma using the manufacturer's recommended membrane capacity. A fresh blood sample containing anti-coagulating agent was used. The hematocrit of the blood sample was adjusted to 50% by aliquoting a known amount of plasma and cells into a microfuge tube. The plasma and cells were mixed well by pulling it on a shaker for 20 minutes. The filter membranes were weighed and then configured for testing (SEE FIG. 3). Pressure was applied by adjusting the screws to provide contact between the membranes. 100 µL of blood was added to the separation membrane, which was allowed to stand for 10 minutes. The collection pad was subsequently weighed again. Plasma volume collected was calculated by taking the difference between the pre and post filtered weights and dividing by the density of plasma. The density of plasma was estimated to be 1025 kg/m$^3$ (Benson K: MCAT review. Emory University 1999:141-199., herein incorporated by reference in its entirety), which is an approximate average value. The plasma recovery was then calculated by dividing the plasma volume collected by the total amount of plasma in the original sample. The separation and collection membrane were disposed off in a biohazard container. The set-up is washed with 70% ethanol, dried and then used for further studies.

Results of experiments performed during development of embodiments of the present invention suggest that VF1 and VIVID GR demonstrated optimal properties for plasma separation and 111, 142 and ACCUWIK Ultra exhibit properties useful in plasma collection (SEE TABLE 1).

TABLE 1

PERCENT RECOVERY OF PLASMA OBTAINED WITH DIFFERENT COMBINATIONS OF SEPARATION AND COLLECTION MEMBRANES.

| Separation Membrane | Collection Membrane | Percent recovery of plasma |
|---|---|---|
| Cytosep | 142 | 43 |
| VF1 | MF1 | 47 |
| VF1 + VF1 | 142 | 64 |
| VF1 + VF1 with Merquot | 142 | 75 |
| VF1 + G934-AH | 111 | 80 |
| Vivid GR | Accuwik | 80 |
| Vivid GR | 142 | 91 |

VF1 + VF1 REFERS TO THE USE OF TWO VF1 MEMBRANES STACKED ON TOP OF EACH OTHER, VH1 WITH MERQUOT REFERS TO THE VF1 CONTAINING MERQUOT, VF1 + G934-AH REFERS TO THE TWO MEMBRANES BEING STACKED ON TOP OF EACH OTHER

The efficiency of separation is governed by several factors. Capillary number or pore size of the collection membrane affects the efficiency of extraction. The smaller the pore size, the greater the efficiency of extraction, which would indicate greater efficiency by the use of 111 membrane compared to 142. While the separation membrane should separate plasma without gelling fouled or clogged, its capacity should be minimal. A membrane with a high liquid capacity would lead to lower efficiency of extraction in the collection membrane.

Figure 4:
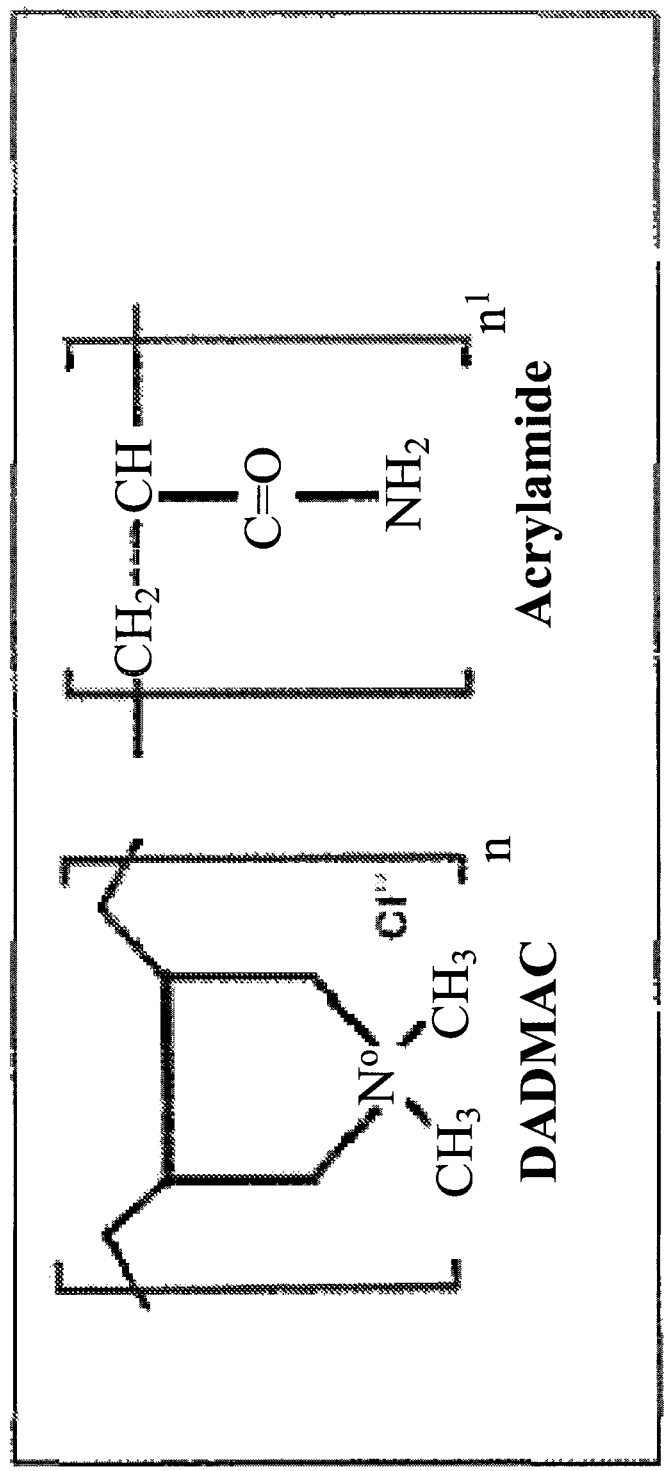
FIG. 4 shows the chemical structure of poly-cation-merquat.
Figure 5:
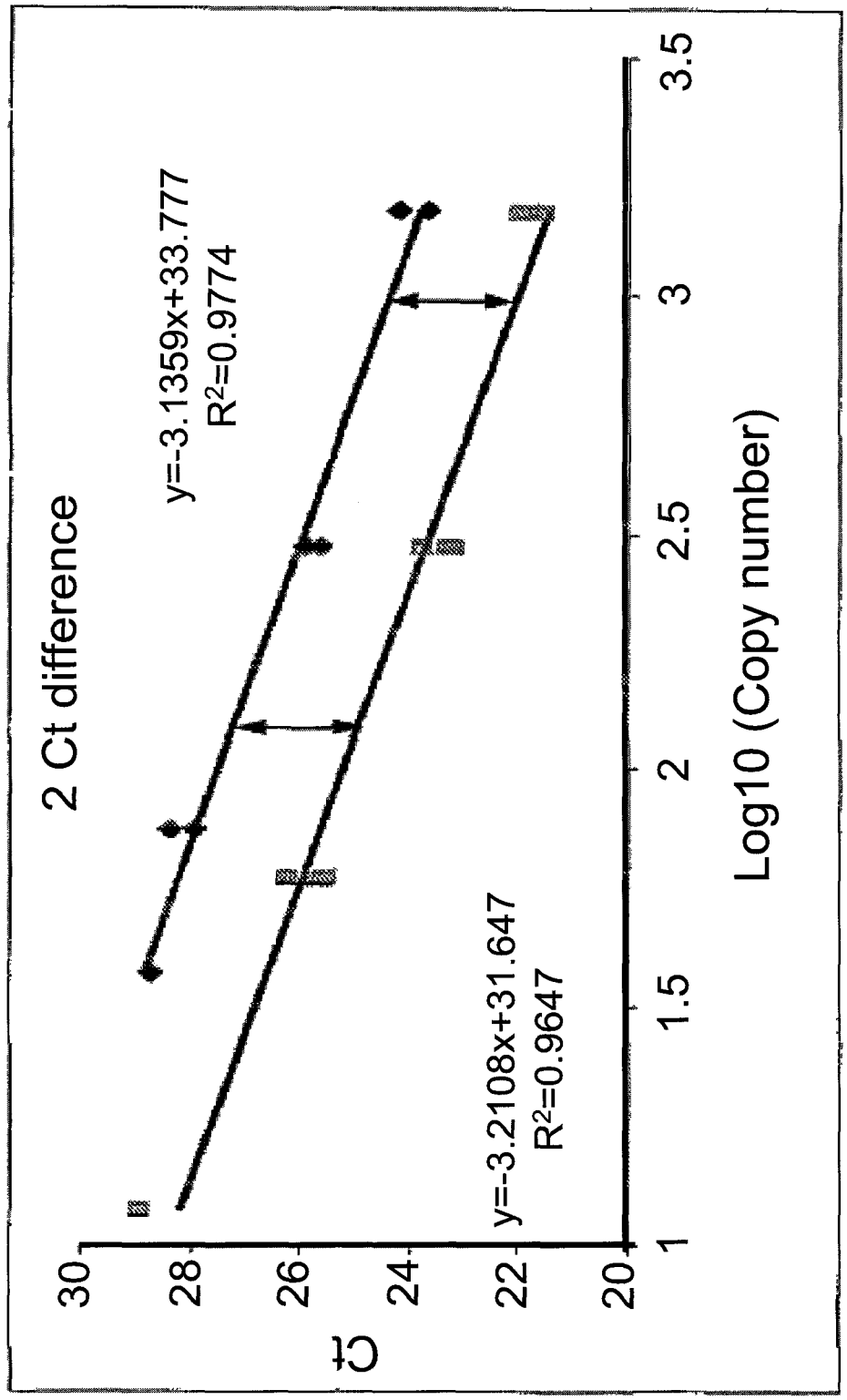
FIG. 5 shows a plot of cycle threshold ($C_T$) verses $\log^{10}$ (copies of HIV-1 viral RNA).: squares denote the $C_T$ values obtained when a plasma samples containing HIV-1 was purified using the IPF method; diamonds denote the $C_T$ values obtained when VF1 was used to separate plasma from whole blood containing HIV-1, and Ahlstrom 142 was used for plasma collection.

The VF1 membrane consists of pores of various sizes and merely retards the flow of membrane. Given sufficiently long times (>10 minutes), the cells eventually leak out of the membrane into the collection pad. The VF1+G934-AH membrane is a combination of a separation pad and a barrier membrane and only works with collection membranes of small pore sizes such as 111. The barrier membrane has a small pore size of 3 µm and prevents the cells from crossing. The VF1 is important to prevent the barrier membrane from getting clogged. Using MF1 as a collection membrane slows down the flow sufficiently to prevent any red blood cells from creeping into the collection membrane, but it reduces the efficiency of extraction as well. As another alternative, the VF1 membrane was submerged in a 2% solution of a polycation, Merquat 550 (Nalco Company, IL) (SEE FIG. 4).

Elution.

Experiments were performed during development of embodiments of the present invention to determine the most suitable membrane for RNA extraction from the sample collection membrane in the lysis/binding buffer. The efficiency of nucleic acid efficiency may be affected by the nucleic acid binding to the RNA in the presence of the lysis/binding buffer containing a high concentration of GuSCN and isopropanol. Membranes with extremely small pore sizes may allow viruses to diffuse into the membrane from the separation membrane, but may not allow the viral RNA from the lysed virus to diffuse out of it once the membrane is submerged in the lysis/binding buffer.

The separation membrane was sized for 50 µL of plasma using the manufacturer's recommendations. HIV-1 virus, acquired from Rush Virology Quality Assurance Laboratory at 1.5×106 copies/mL of plasma, was diluted in seronegative plasma to obtain HIV-1 concentrations of 300 copies/µL. The plasma sample containing HIV was added to the filter membrane and allowed to sit for 5 minutes. The filter membrane was put into a microfuge tube and 600 µL of lysis buffer was added to it and vortex mixed for 10 minutes. Since some of the liquid is absorbed in the filter membrane, 400 µL of the lysis buffer was removed and bead mix consisting of 5 µL of Amblon paramagnetic particles (PMPs) and 5 µL of Binding Enhancer (Applied Biosystem; Foster City, Calif.) was added to it. This solution was vortex mixed for 4 minutes to bind the RNA to the PMPs. The Immiscible Phase Filter (IPF) purification was carried out. HIV-1 viral load quantification was performed using the Abbott Real-Time HIV-1 Amplification Reagent Kit (Huang et al. Nuc Acids Res 2007, 35:e101., herein incorporated by reference in its entirety) (Abbott Molecular, Des Plaines, Ill.) in 25 µL reaction volumes with the addition of 0.2 mg/mL bovine serum albumin (B8667, Sigma), 150 mM trehalose (T9531; Sigma) and 0.2% Tween 20 (28320; Pierce Thermo Fisher Scientific) and 5 µL template. Amplification reactions were performed in Cepheid SmartCycler II (Sunnyvale, Calif.).

All the membranes captured some of the RNA (Table 2). The PALL ACCUWIK retains the least amount of RNA and also shows the least variability of the amount of RNA capture. The glass fiber membranes and the cellulose membranes bind to RNA in the presence of the lysis buffer.

TABLE 2

AVERAGE CYCLE THRESHOLD ($C_T$) AND STANDARD DEVIATION OF $C_T$ OBTAINED BY ELUTION OF VIRAL RNA FROM DIFFERENT FILTER PAPERS IN THE AMBION LYSIS BUFFER, FOLLOWED BY SUBSEQUENT IPG PURIFICATION AND REVERSE TRANSCRIPTASE-POLYMERASE CHAIN REACTION (RT-PCR).

| Collection Pads | Avg Cycle Threshold ($C_T$) | Standard Deviation of $C_T$ |
| --- | --- | --- |
| No membrane | 24.26 | 0.48 |
| Ahlstrom 111 glass fibers | 26.69 | 1.36 |
| Ahlstrom 142 glass fibers | 25.71 | 0.68 |
| Pall Accuwick Ultra | 24.78 | 0.67 |
| Ahlstrom 222 cellulose | 26.86 | 1.09 |
| Pall Cytosep | 26.33 | 1.46 |

NO MEMBRANE REFERS TO A SAMPLE WHERE THE PLASMA SAMPLE WAS ADDED DIRECTLY TO THE AMBION LYSIS BUFFER.

Experiments were performed during development of the present invention to confirm the loss of RNA in Ahlstrom 142. Whole blood containing HIV-1 was separated using the set-up described in FIG. 3. Whatman VF1 was used for separation of cells and Ahlstrom 142 was used for plasma collection. The RNA was extracted and amplified using the protocol described above. As a control, plasma containing HIV-1 was also purified and amplified using the IPF protocol. A 1.5 Ct difference would be expected between the plasma sample and the sample captured on Ahlstrom 142 based on the results shown in Table 2, however, an extra loss of 0.5 Ct was observed (SEE FIG. 4). The additional loss was caused by the loss of viral particles in VF1. A similar study carried out with plasma separated using VF1 containing Merquot gave no results indicating that the virus was captured by the positively charged merquot or the merquot which gets carried over with the plasma inhibits the PCR even after IPF purification.

Example 3

Sample Collection Swabs

Experiments were performed during development of the present invention to examine the use of COPAN sterile swab applicators (Copan Diagnostics Inc., Murrieta, Calif.) as a sample collection device. These swabs use a technology called flocking which entails spraying thousands of short nylon fibers from a perpendicular angle onto the applicator tip. With this approach to the collection, a liquid specimen is absorbed between the adjacent pieces of the nylon strands through capillary action. Specimens are eluted from the swabs once placed in a liquid medium. An additional benefit, aside from greater collection, is that the Flocked Swabs release specimens more rapidly. The swab design includes a texture similar to a velvet brush. While the swabs used for testing were like dip-sticks, the technology could be used to create a membrane surface coated with flocks.

HIV-1 virus, acquired from Rush Virology Quality Assurance laboratory at 1.5×106 copies/mL of plasma, was diluted in seronegative plasma to obtain HIV-1 a concentration of 300 copies/µL. The plasma sample was speared on the swab, and the swab was dipped into a microfuge tube containing 400 µL of Ambion lysis buffer, bead mix was added, and the sample was mixed by vortexing gently for 4 minutes and allowed to stand for an additional 2 minutes. The PMPs were removed using a pick pen and put into a solution containing 200 µL of Ambion lysis buffer also pipetted out from the above microfuge tube. The Immiscible Phase Filter (IPF) purification was carried out. HIV-1 viral load quantification was performed using the Abbott RealTime HIV-1 Amplification Reagent Kit (Abbott Molecular, Des Plaines, Ill.) in 25 µL reaction volumes with the addition of 0.2 mg/mL bovine serum albumin (Sigma), 150 mM trehalose (Sigma) and 0.2% Tween 20 (Pierce Thermo Fisher Scientific) and 5 µL template. Amplification reactions were performed in Cepheid SmartCycler II (Sunnyvale, Calif.).

The swabs are hydrophobic in nature and do not absorb easily. Due to the porous structure of the flocks, it has a low wicking capability. It would however be suitable for more viscous samples. The swab also absorbs RNA and a $C_T$ difference of 2.0 was observed between the samples put on the swab and the positive control where the sample was put into the lysis buffer. This indicates that three-fourth of the RNA was absorbed on the swabs. Washing the swab with water, ethanol or lysis buffer before the test did not change the results. The PMPs also tend to aggregate when they come in contact with the swab. This could be due to the flocks detaching from the swab in the presence of the lysis/binding buffer containing alcohol, salt and detergent, although the present invention is not limited to any particular mechanism of action and an understanding of the mechanism of action is not necessary to practice the present invention.

HIV-1 virus, acquired from Rush Virology Quality Assurance laboratory at 1.5×106 copies/mL of plasma was smeared on the swab. The swab was dipped in 300 µL of Ambion elution buffer (Applied Biosystem; Foster City, Calif.), and allowed to stand for a minute. As much liquid as possible was removed from the swab. 800 µL of Ambion lysis buffer was added to the above stated buffer containing the plasma samples. 800 µL is used instead of 400 µL since the sample volume is large (350 µL). A large volume of elution buffer was used, so that the swab could be completely submerged in the buffer. 20 µL of bead mix containing 10 µL of PMPs and 10 µL of binding enhancer was added. PMPs were removed with a pick pen and moved into 400 uL of lysis buffer. IPF purification was carried out with 50 µL of elution buffer. HIV-1 viral load quantification was performed using the Abbott RealTime HIV-1 Amplification Reagent Kit (Abbott Molecular, Des Plaines, Ill.) in 25 µL reaction volumes with the addition of 0.2 mg/mL bovine serum albumin (Sigma), 150 mM trehalose (Sigma) and 0.2% Tween 20 (Pierce Thermo Fisher Scientific) and 5 µL template Amplification reactions were performed in Cepheid SmartCycler II (Sunnyvale, Calif.) using the Roche TtH. As a positive control, the plasma sample containing HIV-1 virus was added directly to 300 µL of Ambion elution buffer without being applied on a swab. As a negative control, HIV-1 negative plasma is applied to the swab. Controls were processed in the same manner as the samples.

More than half the viral RNA is lost when the samples are collected on the swabs (Table 3). This loss cannot be accounted for by the loss of elution buffer removed with the swab. Some of the RNA or viral particles are absorbed in the swab.

TABLE 3

SAMPLES AND CYCLE THRESHOLD ($C_T$) OBTAINED BY ADDING SAMPLES TO AMBION ELUTION BUFFER, PURIFYING THE RNA USING THE IPF METHOD AND SUBSEQUENT AMPLIFICATION USING THE ABBOTT REALTIME AMPLIFICATION KIT.

| Sample | Cycle Threshold ($C_t$) |
| --- | --- |
| Positive control | 19.75 |
| Sample-1 on swab | 20.91 |

TABLE 3-continued

SAMPLES AND CYCLE THRESHOLD ($C_T$) OBTAINED
BY ADDING SAMPLES TO AMBION ELUTION BUFFER,
PURIFYING THE RNA USING THE IPF METHOD AND
SUBSEQUENT AMPLIFICATION USING THE ABBOTT
REALTIME AMPLIFICATION KIT.

| Sample | Cycle Threshold ($C_t$) |
| --- | --- |
| Sample -2 on swab | 21.2 |
| Negative sample on swab | 0 |

POSITIVE CONTROL DENOTES A PLASMA SAMPLE CONTAINING HIV-1, SAMPLE -1 ON SWAB AND SAMPLE-2 ON SWAB DENOTE PLASMA SAMPLES CONTAINING HIV-1 AND NEGATIVE SAMPLE ON SWAB DENOTES A SERO-NEGATIVE PLASMA SAMPLE ON THE SWAB.

Figure 6:
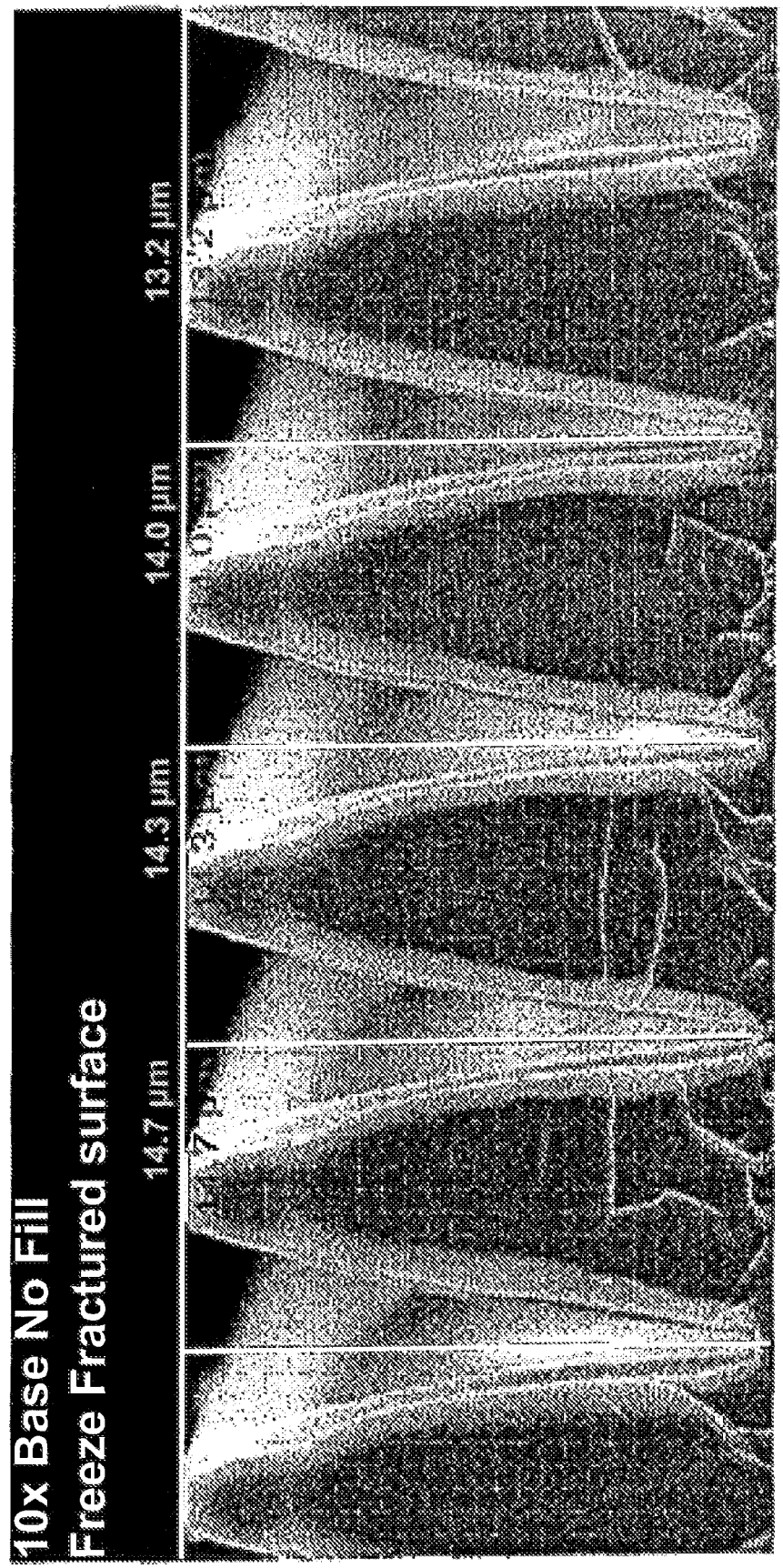
FIG. 6 shows a cross sectional view of pillar chip made by 10× technologies showing pillars which are 14 μm tall and have a base dimension of 151 μm.

The utility of using pillar chips for collection was explored. Pillar chips are symmetric and do not show the variability in pore diameter associated with filter membranes. They are made of plastic and are commonly used as micro-prismatic reflective sheeting for high-brightness traffic signs (10× Technology, Libertyville, Ill.). The technology can be modified to create low-cost pillar chips (e.g., SEE FIG. 6). Preliminary studies showed that their capacity per unit area was low due to the large base diameter and the short height of the pillar, making them unsuitable for a high volume application such as this one. However, pillar chips could find utility in set-ups which require <25 µL of sample.

Example 4

Design Variables

Experiments were conducted during development of embodiments or the present invention to develop a filter paper separation system can effectively separate and collect plasma as well as elute RNA (See, Examples 1-3). The PALL VIVID GR Plasma Separation Membrane and PALL ACCUWIK Ultra Medium filter and collect 80% of the plasma volume contained in the whole blood sample and eluting almost all of the collected RNA for amplification, with less than 0.5 $C_T$ difference when compared to direct plasma sample. Experiments were performed during development of embodiments of the present invention to develop a plasma separation and collection (PSC) unit by optimizing the size of the membranes and the contact pressure between the two membranes using the VIVID GR and ACCUWIK Ultra membranes.

Size of VIVID Membrane.

The VIVID Plasma Separation membrane is an asymmetric, hydrophilic, polysulfone membrane with low biomolecule binding. The asymmetric nature of the material allows the cellular components of blood (red cells, white cells, and platelets) to be captured in larger pores while permitting plasma to flow freely to the other side of the membrane through smaller pores. The cellular components are filtered without lysis, removing their contaminants completely from the plasma sample. Since cellular components are collected within the membrane, it is important to size the VIVID paper so that plasma flow is not hindered by clogged pores. The blood volume capacity of VIVID is defined as the amount of whole blood per square centimeter of medium that can be rapidly and effectively separated with low hemolysis. Blood volume capacity is directly related to the void volume of the material and is defined as 40-50 µL per square centimeter for the GR grade of material. Given the appropriate collection material, the VIVID GR is rated for <80% plasma recovery. An average patient with 50% hematocrit would need to supply 125 µL of whole blood to be able to collect 50 µL of plasma. Therefore, to ensure that no clotting or lysis occurs, the VIVID membrane must be 2.5 square centimeters in area which corresponds to an 18 mm diameter circular punch.

Size of ACCUWIK Membrane.

The ACCUWIK is used to collect the fixed amount of plasma. The absorption capacity as defined by Pall Life Sciences is 38 µL per square centimeter, which corresponds to a 12.9 mm diameter circular punch for a 50 µL plasma sample. This small size of the ACCUWIK relative to the size of the separating membrane (VIVID) allows concentration the plasma into a small volume. The porous ACCUWIK provides a matrix for easy transport of liquid and for further chemical assays within the matrix.

Experiments were performed to further confirm the useful size for the ACCUWIK membrane. The absorbance capacity of the ACCUWIK Ultra was measured in µL per square centimeter by adding a fixed volume of plasma and measuring the resulting welled area. The ACCUWIK Ultra medium is a hydrophilic fibrous membrane made out of hydroxyiated polyester and characterized by uniform uptake and rapid release. ACCUWIK strips were cut using a commercially available paper cutter. The width of each strip was measured and recorded. The length of each strip was approximately 100 mm. 50 µL of plasma was added to the end of the strips and allowed to wick laterally until the front edge stopped moving. The length of the welled area was measured and recorded. 100 µL of plasma was added to the end of a second set of strips and allowed to wick laterally until the front edge stopped moving. The length of the welled area was measured and recorded. To determine the absorption capacity, the plasma volume (50 or 100 µL) is divided by the total welled area, which is calculated by multiplying the welled length by the strip width. The absorption capacities in µL per square centimeter for the two sets of test strips were averaged. While the reported capacity of the ACCUWIK Ultra medium was 38 µL/mm$^2$, the calculated average value from the experimental testing suggest that the capacity is actually slightly greater at 44.5±2.2 µL/mm$^2$. Using this absorbance capacity for the membrane, a 12 mm diameter round punch would be needed to hold the required plasma volume of 50 µL.

Example 5

Plasma Collection and Separation Module

The plasma collection and separation unit comprises two parts: the cell separation module and the plasma module. The cell separation module houses the VIVID filter, while the plasma module contains the ACCUWIK membrane (SEE FIG. 7). Once assembled, the ACCUWIK membrane lies in direct contact with the VIVID filter, providing capillary force to wick the plasma from the membrane. The contact pressure is established by the positioning of the plasma module with respect to the cell separation module. The whole blood sample is added through the opening in the top of the device and placed directly on the VIVID membrane. After an adequate amount of time has passed the plasma module is unscrewed from the cell separation module and inserted into the test cartridge for further processing. The cell separation module containing the filtered material can then be properly discarded.

Figure 8:
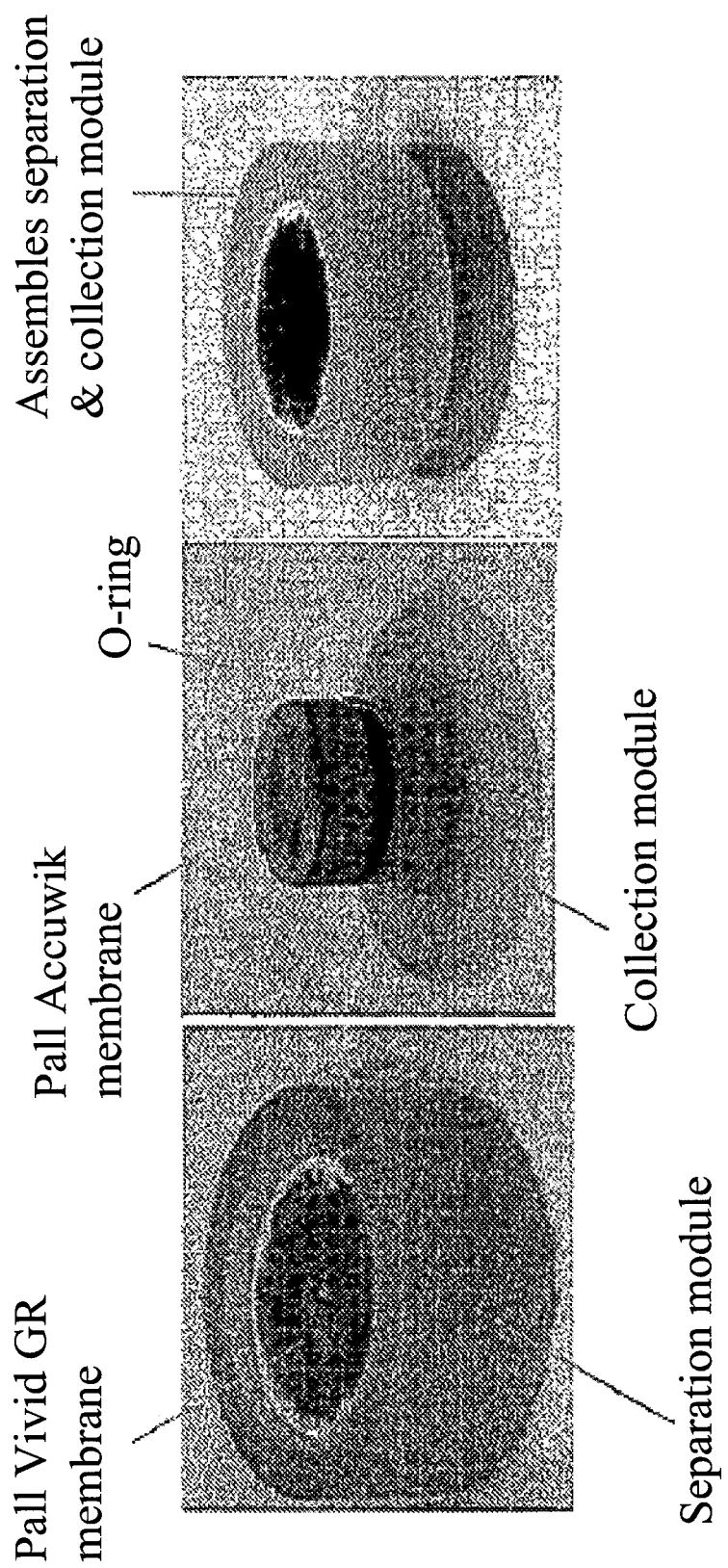
FIG. 8 shows an exemplary first generation plasma separation and collection module: (left) PALL VIVID GR cell separation membrane attached to separation module; (center) PALL ACCUWIK plasma collection membrane attached to collection module; (right) cell separation and collection module attached to each other for plasma separation from whole blood.

The first generation system was machined out of polypropylene (SEE FIG. 8). Polypropylene was selected because it is chemically inert. However, polypropylene does exhibit poor machining properties. The filter membrane is attached to the modules by a double sided adhesive. While several methods of adhesion may find use with a device of the present invention, e.g., sonic welding, heat sealing, laser welding, mechanical clamping, etc, adhesive was selected for the first generation device as it allows the plastic module to be reused. The adhesive exhibited excellent bond strength to most surfaces including low surface energy plastics such as polypropylene. The O-ring in the collection module forms a tight seal and holds the two modules together due to a friction fit. Preliminary studies conducted during development of embodiments of the present invention demonstrated that it was difficult to accurately control the contact between the two membranes in this set-up which led to variable plasma separation efficiency. Contact pressure was therefore identified as a key parameter to be optimized for consistent and efficient plasma separation.

Figure 9:
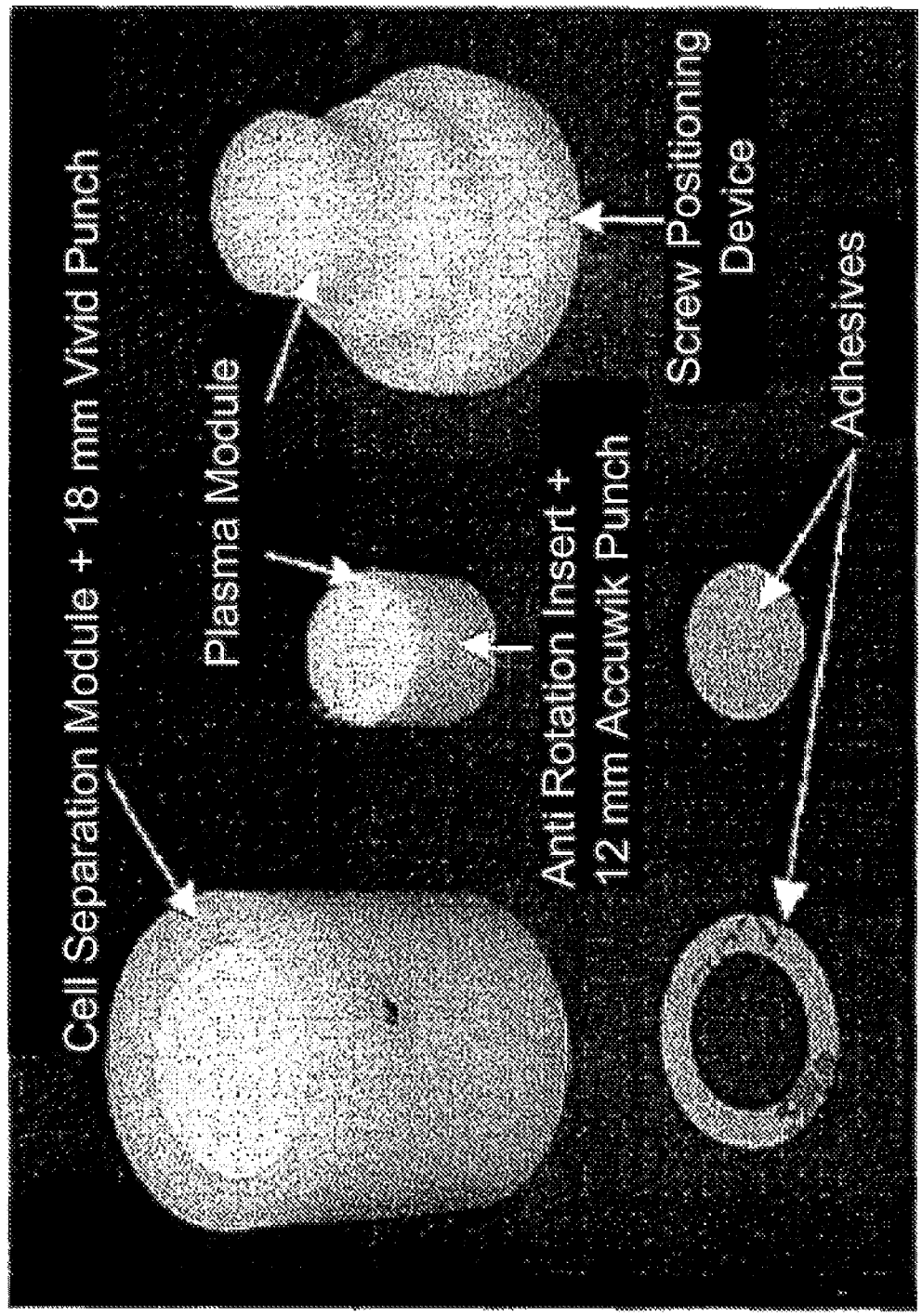
FIG. 9 shows an exemplary second generation plasma separation and collection modules: (left to right) the cell separation module attached to PALL VIVID membrane with the adhesive, the anti-rotation insert attached to the PALL ACCUWIK, and the screw positioning device.
Figure 10:
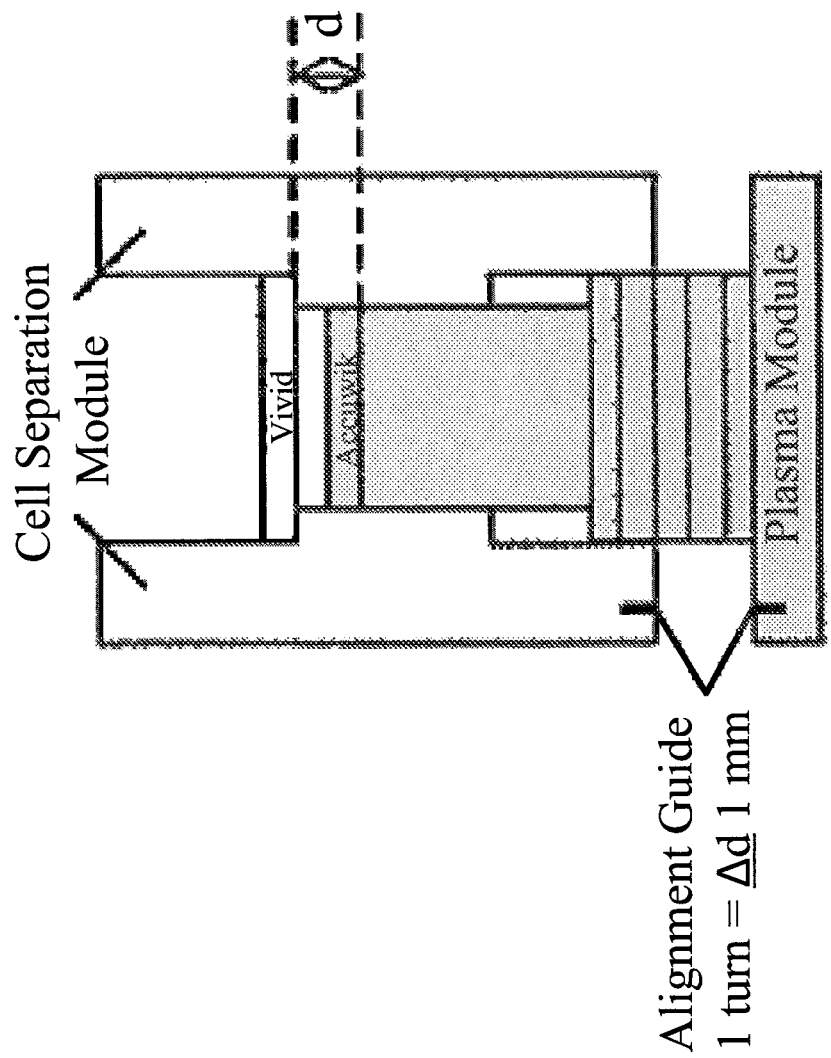
FIG. 10 show a positioning mechanism for blood-plasma unit pressure studies.

Second generation modules were machined out of polypropylene to integrate a screw lock mechanism which allowed for accurate positioning of the filter membrane with respect to each other (SEE FIG. 9). In order to prevent the membranes from getting compromised by shearing as the plasma module is screwed into the collection module, an anti-rotation insert was designed (SEE FIG. 9). The cell separation module has a fastening dowel pin projecting inwards. The anti-rotation insert has a notch in which the dowel pin sits. This prevents the anti-rotation insert from rotating, but allows it to move up and down freely. The vertical motion is still achieved by rotating the screw positioning device shown in the figure. Each cell separation module and the corresponding screw position device are labeled to allow the two to be coupled. When completely screwed together, the distance d shown in FIG. 10 is 1 mm. At this point the numbers engraved on the cell separation module and the corresponding screw module device lie on the same vertical axis. When the matched numbers are screwed together, the distance "d" is maintained.

Example 6

Pressure

Experiments were conducted during development of embodiments of the present invention to determine the optimal positioning of the ACCUWIK membrane with respect to the VIVID membrane so that contact is maintained at all times and the optimal pressure is applied at the filter paper interface. The optimal filter paper placement was defined as the position that yields the highest volume of plasma collected with the smallest variability between tests.

Filter papers and adhesives were cut to the appropriate size using a laser cutter machine. Cell separation and plasma modules were washed in 70% EtOH and allowed to dry. The 12 mm round adhesive cut out was used to adhere the 12 mm ACCUWIK cut out to the anti rotation insert. The anti-rotation insert and ACCUWIK were weighed on a balance and the weight was recorded. The anti-rotation insert was then placed in the cell separation module and the screw positioning piece was screwed into the cell separation module from the bottom. Etched numbers on both the cell separation module and screw positioning piece were used to establish position with one full turn corresponding to 1 mm of vertical movement. The anti-rotation piece was first placed well below the VIVID platform on the cell separation module to allow the 18 mm VIVID cut out to be adhered. The 18 mm adhesive ring was used to adhere the 18 mm VIVID to the cell separation module using the edges as a guide. The screw positioning device was then used to position the ACCUWIK at distances of −0.5 mm, 0 mm, 0.25 mm and 0.5 mm from the bottom surface of the VIVID membrane. The distance, d, is defined as the distance between the bottom surface of the VIVID and the top surface of the anti rotation piece (bottom surface of the ACCUWIK) (SEE FIG. 10). The upward direction is negative. 125 µL of whole blood (50% Hematocrit) was added to the VIVID. 50% hematocrit was achieved by spinning whole blood samples in a centrifuge (4000×) for 10 minutes, transferring all of the plasma to a new tube and adding the same volume of cellular components to the plasma sample. Enough 50% hematocrit blood was prepared so that the same blood source was used for all tests. The sample was allowed to filter for 10 minutes. The VIVID membranes were then removed and properly discarded in a biohazard container. The anti-rotation piece was also removed and weighed on the balance. The weight was recorded. The ACCUWIK membrane was then disposed of in a biohazard container. Plasma volume collected was calculated by taking the difference between the pre and post filtered weights and dividing by the density of plasma. The density of plasma was assumed to be 1025 Kg/m$^3$. The plasma recovery was then calculated by dividing the plasma volume collected by the total amount of plasma in the original sample, which in this instance was 57.5 µL, and multiplying by 100.

The 0 mm and 0.25 mm distances produced the highest plasma recovery of 52 µL and 53 µL. However, at a distance of 0.25 mm, the variability (standard deviation) was 5.9111 compared to 0.9411 at 0 mm. At the 0.5 mm distance, the ACCUWIK membrane (thickness=0.38-0.53 mm) may no longer be in contact with the VIVID membrane and therefore, does not collect as much plasma as a result of the decrease in capillary force. At the −0.5 mm distance (meaning the ACCUWIK is fully compressed against the VIVID), a high plasma recovery was observed; however, the plasma recovery was not as high at the other two distances. This is most likely due to large reduction in void volume caused by the compression of the material fibers, although the present invention is not limited to any particular mechanism of action and an understanding of the mechanism of action is not necessary to practice the present invention. Based on the experiments conducted during development of embodiments of the present invention, a distance of 0 mm was used for examples 7-13.

Example 7

Effects of Sample Variables

Experiments were conducted during development of embodiments of the present invention to determine the effect of blood volume on plasma collection with methods, systems, and devices of the present invention. The volume of blood obtained from a particular lancing device is dependent on three major factors: physical/mechanical (e.g., the lancing device itself), biological (e.g., the thickness of the skin, the subject's hematocrit, the subject's weight, the amount and potency of clotting factors in the subject's blood, etc.), and process (e.g., position of lancet, ability to maintain good contact between the lancet and the skin during the lancing process, etc.). While the volume of blood collected is variable, in some embodiments, methods, systems, and devices must collect constant volume of plasma in order to quantitatively measure the constituents of plasma, e.g., HIV-1 viral copies in plasma.

Commonly in the art, an aliquot of plasma is taken for testing, after it has been separated from blood by centrifugation. However, this complicates a procedure; generally requires the use of two devices: 1) a centrifuge for separation the blood from the plasma, and 2) precision equipment to measure plasma; and renders a procedure in adequate for use in the field. Therefore, in some embodiments, the present invention provides a simple, low-cost, device to collect a fixed amount of plasma, independent of the volume of the original sample (e.g., the amount of blood obtained from a finger stick).

Figure 11:
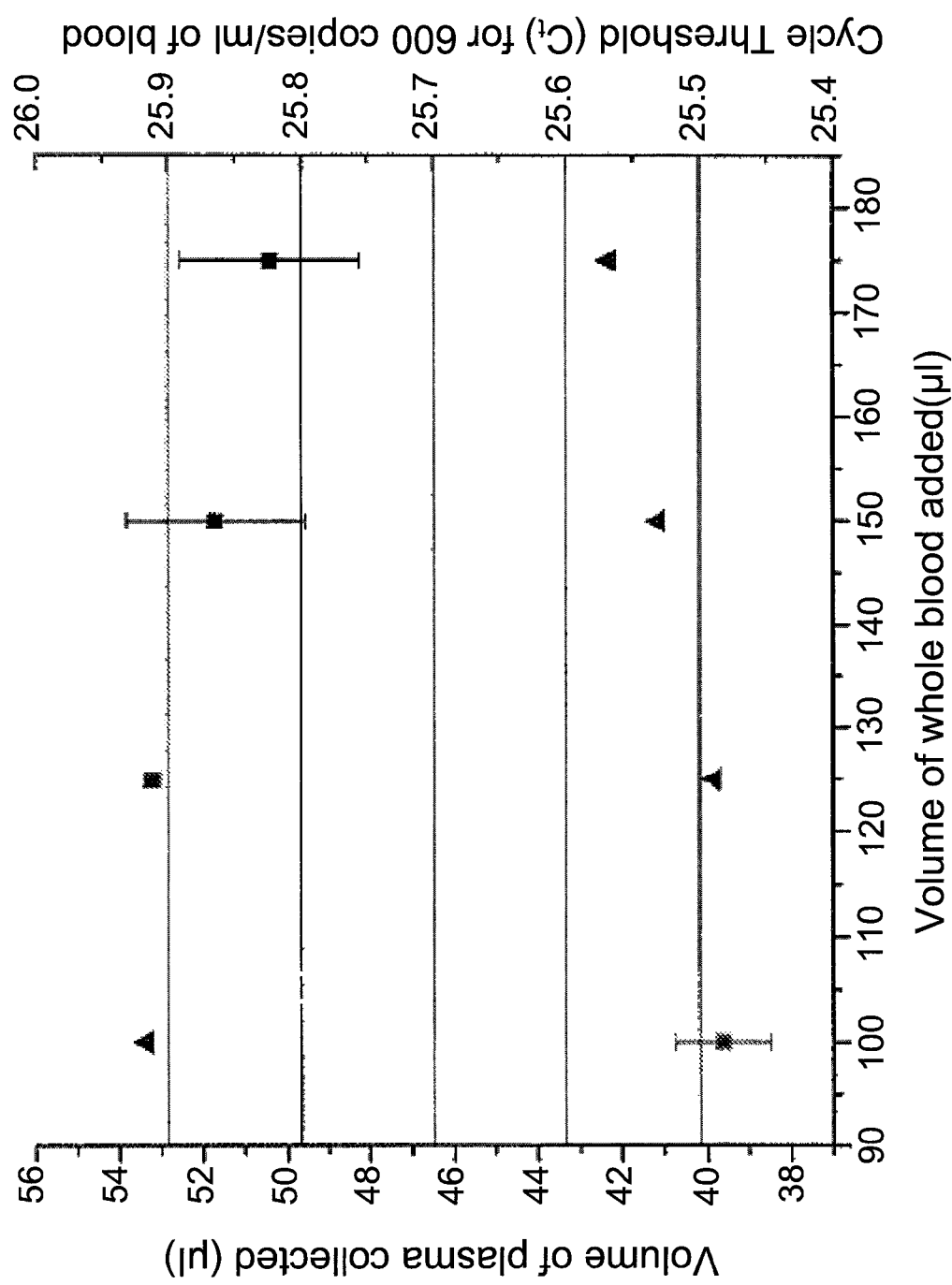
FIG. 11 shows a plot of the volume of plasma collected (squares) and estimated cycle threshold for 600 copies of hiv-1 virus per mL of blood (triangles) versus volume of whole blood added to the blood-plasma unit.

In some embodiments, the present invention provides a wick (e.g., ACCUWIK) which is sized to collect a fixed amount of plasma, leaving the rest of the plasma on the VIVID GR membrane. In some embodiments, the present invention provides a low cost device which permits blood to be collected directly onto a filter paper, rather than a capillary tube, Experiments were conducted during development of embodiments of the present invention to demonstrate that a device of the present invention would collect a fixed amount of plasma independent of the amount of blood added. Fresh blood from a human subject was used for the study. A known volume of blood with a hematocrit level of 45% was added to the device. The device was allowed to stand for 10 minutes, and the volume of plasma collected was measured. 100, 125, 150 and 175 µL of blood was added to devices and the plasma volume was measured (SEE FIG. 11). Addition of less than 125 µL yielded collection of 39.6 µL of plasma, at an efficiency of 88.1%. Therefore, a minimal volume of 125 µL is required to collect 50 µL of plasma. Addition of increasing blood volume up to 175 µL did not lead to an increase in volume of plasma collected. The maximal efficiency of plasma collection of 94.6% is obtained on addition of 125 µL of plasma, which reduces with increasing volume of blood. FIG. 11 also shows the effect of the variability of plasma collection levels on the Cycle Threshold for 600 copies of HIV-1/mL of blood. This was estimated by using the standard curve of HIV-1 (y=−3.33x+31.5) obtained by purifying different concentrations of virus in plasma and amplifying it. In some embodiments of the present invention, 600 copies/mL is the lower limit of detection, therefore, the effect of volume change on $C_T$, would be highest at this number. $C_T$ changes from 25.49 to 25.56, when the blood added to the blood-plasma device changes from 125 µL to 175 µL. This is well within the accepted range of +0.5 specified for our test device.

Figure 12:
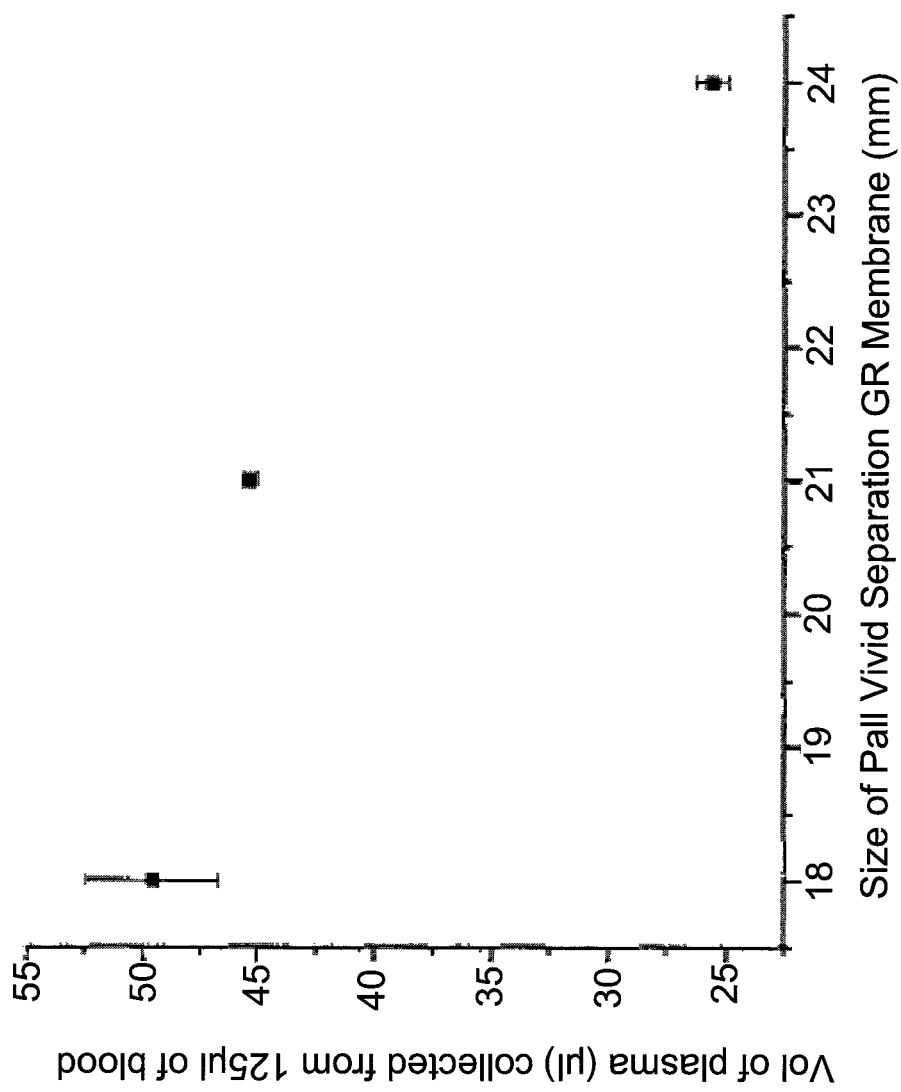
FIG. 12 shows a plot of the volume of plasma collected on the PALL ACCUWIK membrane (plasma collection module) on the addition of 125 μL of blood to the blood-plasma unit at three different vivid membrane sizes.
Figure 13:
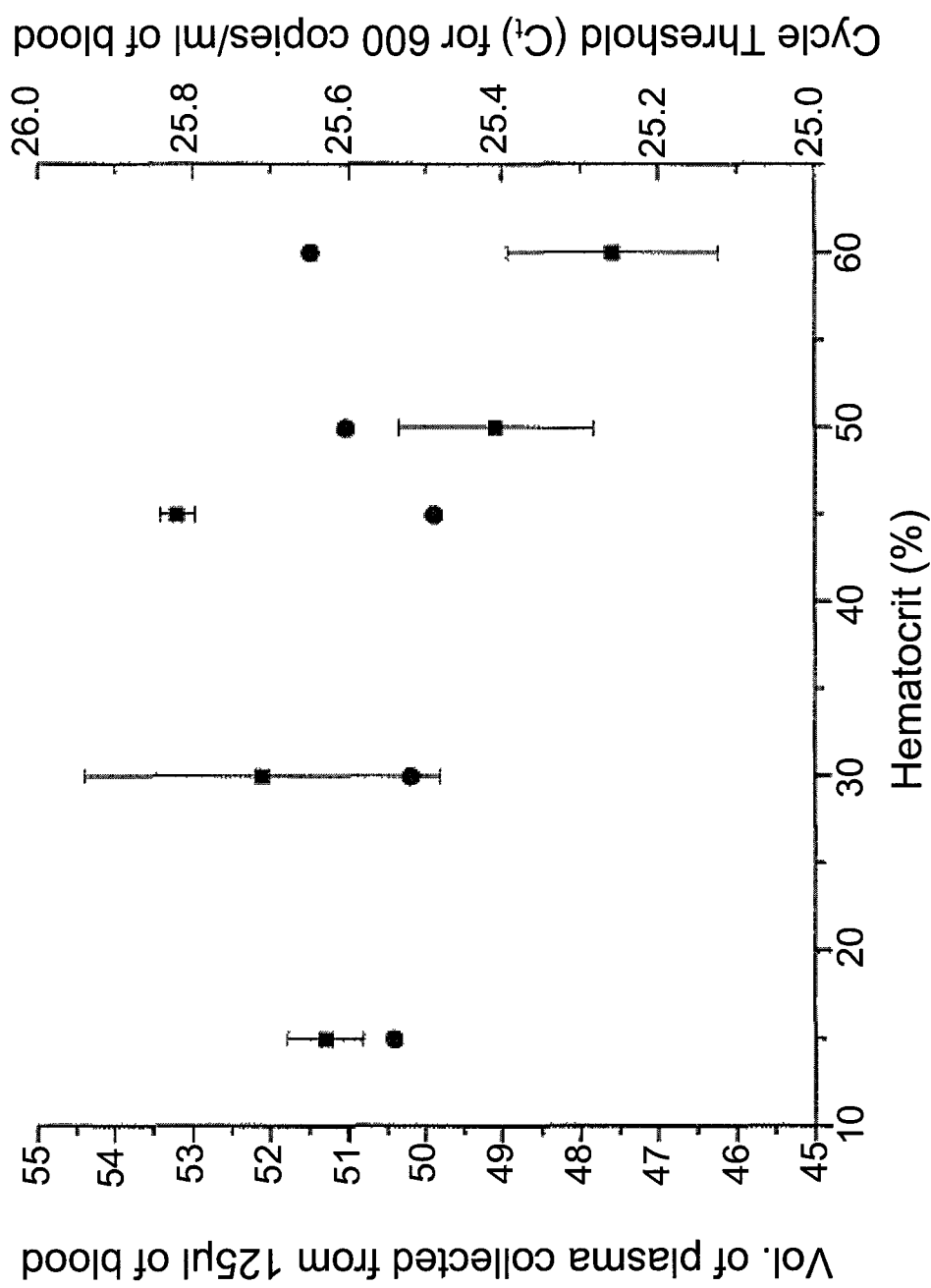
FIG. 13 shows a plot of the volume of plasma collected (squares) and estimated cycle threshold for 600 copies of HIV-1 virus per mL of blood (circles) versus hematocrit levels in blood (%).

Experiments were conducted during development of embodiments of the present invention in which the VIVID Plasma Separation GR membrane was sized as per the manufacturer's protocols, and different sizes of PALL VIVID membrane were tested while maintaining the optimized contact pressure between the VIVID and the ACCUWIK membrane, and the size of the ACCUWIK membrane (SEE FIG. 12). Increasing the size of the membrane reduces the efficiency of purification. In all test set-ups, the plasma collection module was separated from the separation module 10 minutes after the addition of the blood to the blood plasma unit.

In some embodiments, experiments were conducted to determine the effect of hematocrit on plasma collection. The hematocrit is the proportion, by volume, of the blood that consists of red blood cells. A normal hematocrit level varies significantly with gender, age, health, etc. Given a fixed volume of blood, changes in hematocrit levels affect the amount of available plasma for purification. It also affects the viscosity of the blood, thereby affecting flow rate through a device. The PALLVIVID Plasma Separation GR membrane is a highly asymmetric membrane which separates red blood cells from plasma by size exclusion filtration. Therefore, high hematocrit levels can clog up the membrane leading to poor plasma separation. Experiments were performed to determine the effect of such changes in hematocrit on the plasma collection volume from a fixed volume of whole blood. A device of the present invention was set up as described previously, and blood from a single subject was centrifuged at 3500 rpm for 20 minutes to separate the cells. The plasma levels were adjusted to create blood samples with 5 different hematocrit levels between 15-60%. 125 µL of the blood sample was then added to the blood-plasma module and the volume of plasma collected on the plasma module was measured. The volume changes from 53.2 µL to 47.6 µL at the five different hematocrit levels, corresponding to an estimated $C_T$, change of 0.16 at a concentration of 600 copies/mL of HIV-1, estimated by using the standard curve of HIV-1 (y=−3.33x+31.5) obtained by purifying different concentrations of virus in plasma and amplifying it. The results show that the blood-plasma module can successfully separate plasma at different hematocrit levels without any clogging of the VIVID Plasma Separation GR membrane. The volume of plasma collected drops with increasing hematocrit due to reduced amount of plasma in the sample. At a hematocrit level of 60%, 125 µL of blood contains only 50 µL of plasma. Therefore, the collected plasma is also lower. At a hematocrit level of 15%, the available plasma is 106.25 µL. However, only 51.3 µL collects in the plasma module, since the PALL ACCUWIK membrane is saturated and does not allow more plasma to flow into the module.

Example 8

Fresh Whole Blood Separation

Experiments were conducted during development of embodiments of the present invention to demonstrate the effectiveness of the plasma separation and collection module to efficiently separate plasma from whole blood obtained from different human patients. Since blood is an extremely complex matrix, its variability from person to person may affect its rheological and flow properties through the membrane which in turn would affect the sample purification efficiency.

Figure 14:
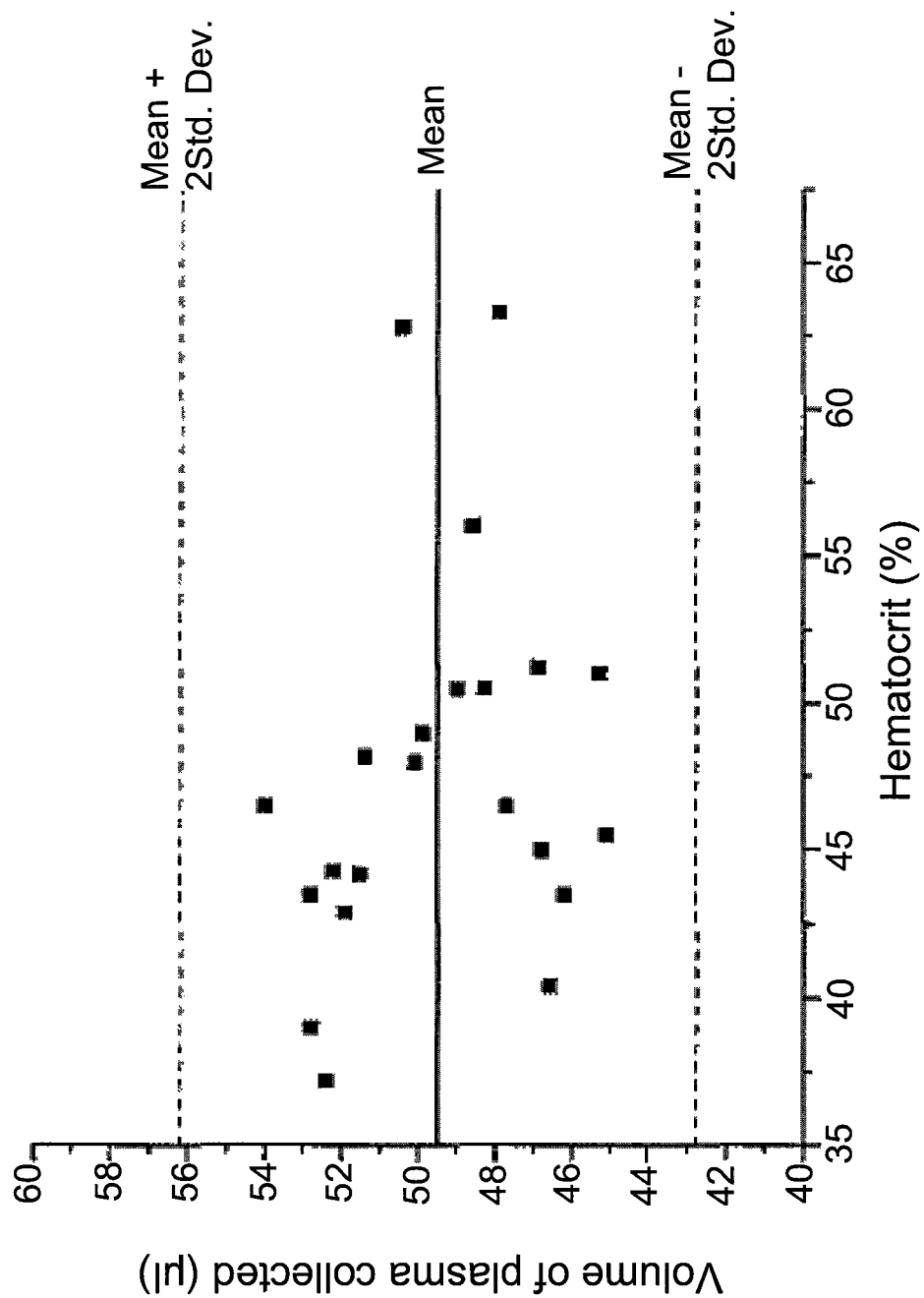
FIG. 14 shows a plot of volume of plasma separated (μL) from 125 μL of whole blood using the plasma separation and collection module verses the blood hematocrit (percentage). Squares denote the average amount of plasma obtained from a different blood sample measured in duplicates. The solid line denotes the mean volume of blood collected from all the samples and the dashed lines show the mean±2 standard deviations.

Fresh blood was obtained from Northwestern Memorial Hospital for this study. The blood sample was made homogenous by putting the tube on a rotating shaker for 2 minutes. The hematocrit of the blood samples was measured by spinning 30 µL of the blood in a Light Cycler PCR Tubes (F. Hoffmann-La Roche Ltd, Basel, Switzerland) at 3000 rpm for 10 minutes. The hematocrit was measured. 125 µL of blood was added and plasma was collected. The plasma separation and collection module successfully separated plasma from different blood samples (SEE FIG. 14). The average volume of plasma collected from 125 µL of plasma was 49.5 µL. The standard deviation of the volume of plasma collected is 3.35 µL. It was observed that the separation efficiency was significantly better with freshly collected blood and decreased as the blood sample got older. All tests were carried out with blood samples collected by venal puncture in a vacuum tube containing an anti-coagulant.

Experiments were conducted during development of embodiments of the present invention to test the effectiveness of plasma separation and collection blood containing high white blood cell count. 53 µL of plasma was successfully collected from 125 µL of whole blood suggesting that high white blood cell count does not clog the membrane. The testing was carried out using the protocol described above.

Example 9

Viral Load Measurement from Whole Blood

Experiments were conducted during development of embodiments of the present invention, in which viral load measurement was used to demonstrate feasibility of plasma separating system for clinical applications. This objective was to separate blood cells from plasma, concentrate the plasma on a smaller ACCUWIK disc and hence forth use it for HIV-1 viral RNA extraction, purification and PCR based detection without a significant loss in RNA in the separation and collection modules. Plasma was separated from whole blood using either a device of the present invention of standard laboratory centrifugation.

Samples for either processing technique were prepared by separating blood cells and plasma from blood, by centrifugation at 3500 rpm for 10 minutes. The proportion of cells and plasma to be mixed together to reconstitute a blood sample with a hematocrit percentage of 45 was calculated. Plasma was spiked with HIV-1 virus obtained from Northwestern Memorial Hospital (stock concentration of 1500 copies/µL of plasma) to obtain a concentration of 300, 60 and 12 copies/µL respectively. Blood was reconstituted using this plasma and cells by mixing them in a proportion 45% cells and 55% plasma.

For samples processed by a device of the present invention, 125 uL of the above blood was added to the VIVID membrane of the plasma collection and separation module and allowed to stand for 10 minutes to allow the plasma to separate. The VIVID was carefully removed. The ACCUWIK was inserted into a microfuge tube (Tube-1) containing 400 µL of Ambion Lysis buffer containing Ambion Binding/Lysis Concentrate, isopropyl alcohol and Ambion Carrer RNA.

For samples processed by standard laboratory centrifugation, blood was centrifuged at 3000 rpm for 10 minutes to separate the plasma from the cells. 50 µL of plasma was then added to the ACCUWIK of the same size as used for the plasma separation and collection module. The ACCUWIK is inserted into a microfuge tube containing Ambion Lysis buffer containing Ambion Binding/Lysis Concentrate, isopropyl alcohol and Ambion Carrier RNA.

Figure 15:
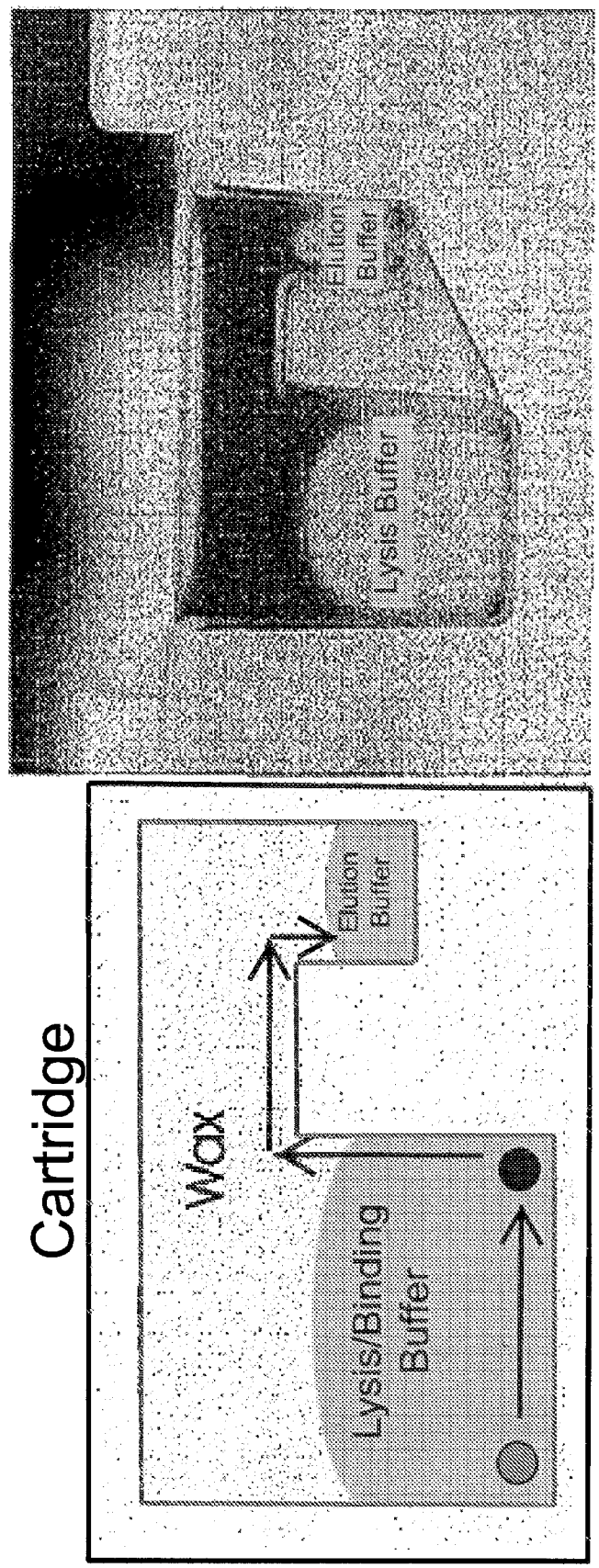
FIG. 15 shows a schematic of the IPF process (left): the PMPs bind to the NA and are moved by an external magnet from the lysis buffer to the elution buffer through liquid wax; (right) molded cartridge containing lysis buffer, elution buffer, and a colored liquid wax.
Figure 16:
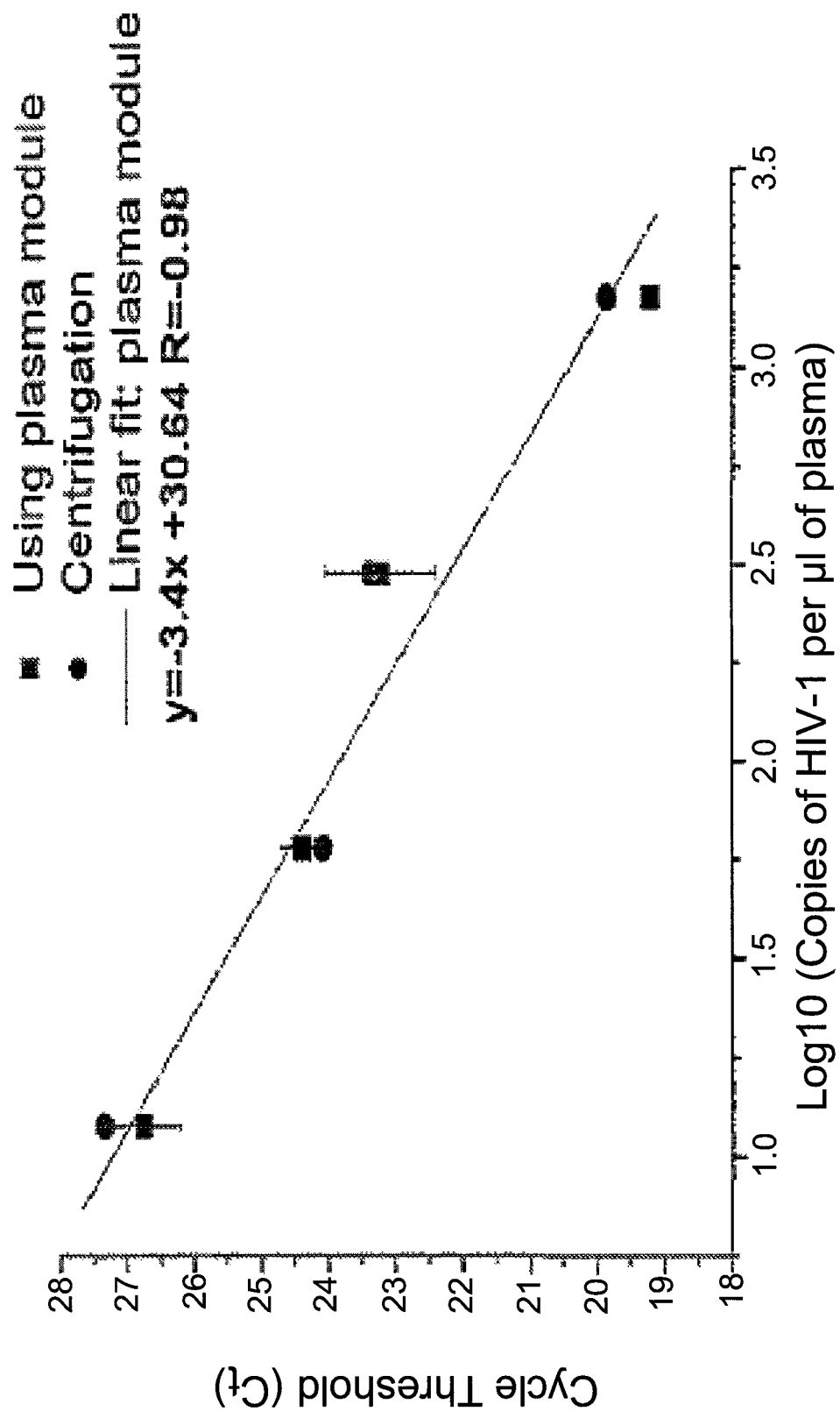
FIG. 16 shows a plot of cycle threshold ($C_T$) verses $\log^{10}$ (copies of HIV-1 per μL of plasma. Squares denote samples separated using the plasma separation and collection module, and the ovals denote spots separated using centrifugation.

All samples were then vortex mixed for 2 minutes. 10 µL of Bead Mix containing Ambion PMPs and Ambion binding enhancer was added and vortexed again for 4 minutes. 200 µL of the solution was pipetted out and transferred to another tube (Tube-2). The PMPs were carefully removed using a Pickpen-1 Magnetic tool (Sunrise Science Products Inc, San Diego, Calif.) and put into the other tube as well. The remaining solution in the first tube was eliminated. The sample in Tube-2 was then processed using the IPF method (SEE FIG. 15). The sample from Tube-2 was added to the larger chamber of the cartridge and mixed for 4 minutes using the automated system. 50 µL of elution buffer was aliquoted into the smaller chamber of the IPF cartridge and the two aqueous fluids were overlaid as shown in FIG. 15. The automated system aggregated the PMPs for 2 minutes using the external magnet and moved the aggregate from the lysis buffer to the elution buffer. The elution buffer containing the PMPs was heated to 55° C. for 10 minutes to elute the RNA. The PMPs were aggregated and removed from the elution buffer. HIV-1 viral load quantification was performed using the Abbott RealTime HIV-1 Amplification Reagent Kit (Abbott Molecular, Des Plaines, Ill.) in 25 µL reaction volumes with the addition of 0.2 mg/mL bovine serum albumin (B8667, Sigma), 150 mM trehalose (T9531; Sigma) and 0.2% Tween 20 (28320; Pierce Thermo Fisher Scientific) and 5 µL template. Amplification reactions were performed in Cepheid SmartCycler II (Sunnyvale, Calif.). Each viral load was run in quadruplets.

A PCR efficiency of E=96.84% was observed, suggesting that the plasma separation was efficient without carryover of red-blood cells which inhibit the PCR. The results obtained from centrifugation of blood and from separation using the plasma separation and collection modules were identical, demonstrating that there was no significant loss in viral particles in the filler membrane.

Example 10

PMP Storage in Membrane Matrix

Experiments were conducted during development of embodiments of the present invention to demonstrate the feasibility of storage of PMPs in the ACCUWIK membrane. In some embodiments, the plasma containing the HIV-1 virus is separated into the ACCUWIK membrane through the VIVID membrane. This membrane is subsequently inserted into the tube containing the lysis buffer, whereby the virus is lysed and the viral RNA binds to the PMPs. The viral RNA diffuses out of the paper into the lysis buffer containing the PMPs. In order to facilitate the process, the solution containing the paper is agitated. A portion of the RNA is lost in the paper due to absorption on the membrane fibers. In some embodiments, to minimize the loss of RNA in the filter membrane and eliminate the need for agitation, the PMPs are pre-dispensed in the ACCUWIK. When a sample containing viral RNA is added to the paper, the virus and the PMPs are both located in the porous matrix of the ACCUWIK membrane. On addition of lysing reagents, the viral RNA can immediately bind to the PMPs without having to diffuse out of the paper. The membrane therefore acts as a matrix for reagent storage and subsequent RNA capture. In order to further process the sample, the magnetic particles are extracted out of the paper using an inexpensive permanent magnet or an electro-magnet. This process eliminates the need for agitation, heating and centrifugation associated with the extraction of RNA from filter. Also, it provides a convenient location for reagent storage for point of care applications.

In experiments conducted during development of embodiments of the present invention, PMPs from the Ambion Magmax kit were aliquoted in a microfuge tube and put on a magnetic stand to collect the PMPs. The liquid was removed and the PMPs were re-suspended in Ambion Binding Enhancer. For each test sample, 10 µL of PMPs and 10 µL of Ambion Binding Enhancer were used. A 5 µL solution containing 4% BSA and 0.4% Triton-X is added. The solution was added to a 12 mm ACCUWIK Ultra disc having an area sufficient to hold 50 µL of sample and allowed to air dry for 3 days at room temperature. Plasma was spiked with HIV-1 virus obtained from Northwestern Memorial Hospital (stock concentration of 1500 copies/µL of plasma) to obtain a concentration of 300, 60 and 12 copies/µL, respectively. The air dried ACCUWIK Ultra was inserted into a microfuge tube (Tube-1) and 50 µL of plasma sample were added to the paper. 400 µL of Ambion lysis buffer was added to the solution and this solution was allowed to sit for 6 minutes. The magnetic particles were removed from Tube-1 using a Pickpen-1 Magnetic tool (Sunrise Science Products Inc, San Diego, Calif.) and transferred to 400 μL of Ambion Wash Buffer-1 in Tube-2. The sample in Tube-2 was then processed using the IPF method (SEE FIG. 15). The sample from Tube-2 was added to the larger chamber of the cartridge and mixed for 4 minutes using the automated system. 50 μL of elution buffer was aliquoted into the smaller chamber of the IPF cartridge and the two aqueous fluids were overlaid with CHILLOUT liquid wax (Biorad laboratories; SEE FIG. 15). The automated system aggregated the PMPs for 2 minutes using the external magnet and moved the aggregate from the lysis buffer to the elution buffer. The elution buffer containing the PMPs was heated to 55° C. for 10 minutes to elute the RNA. The PMPs were aggregated and removed from the elution buffer. HIV-1 viral load quantification was performed using the Abbott RealTime HIV-1 Amplification Reagent Kit (19J (Abbott Molecular, Des Plaines, Ill.) in 25 μL reaction volumes with the addition of 0.2 mg/mL bovine serum albumin (B8667, Sigma), 150 mM trehalose (T9531; Sigma) and 0.2% Tween 20 (28320; Pierce Thermo Fisher Scientific) and 5 μL template. Amplification reactions were performed in Cepheid SmartCycler II (Sunnyvale, Calif.).

For fresh samples, plasma was spiked with HIV-1 virus obtained from Northwestern Memorial Hospital (stock concentration of 1500 copies/μL of plasma) to obtain a concentration of 300, 60 and 12 copies/μL respectively. 50 μL of the plasma sample containing different concentrations of HIV-1 virus was added to a microfuge tube (Tube-1). 400 μL of Ambion lysis buffer was added to Tube-1 and vortex mixed for 30 seconds. 20 ul of bead mix containing 10 μL of PMPs and 10 ul of binding enhancer was added and vortex mixed for 4 minutes. The magnetic particles were removed from Tube-1 using a Pickpen-1 Magnetic tool (Sunrise Science Products Inc, San Diego, Calif.) and transferred to 400 μL of Ambion Wash Buffer-1 in Tube-2. The sample in Tube-2 was then processed using the IPF method (SEE FIG. 15). The sample from Tube-2 was added to the larger chamber of the cartridge and mixed for 4 minutes using the automated system. 50 μL of elution buffer was aliquoted into the smaller chamber of the IPF cartridge and the two aqueous fluids were overlaid with CHILLOUT liquid wax (Biorad laboratories; SEE FIG. 15). The automated system aggregated the PMPs for 2 minutes using the external magnet and moved the aggregate from the lysis buffer to the elution buffer. The elution buffer containing the PMPs was heated to 55° C. for 10 minutes to elute the RNA. The PMPs were aggregated and removed from the elution buffer.

HIV-1 viral load quantification was performed using the Abbott RealTime HIV-1 Amplification Reagent Kit [19] (Abbott Molecular, Des Plaines, Ill.) in 25 μL reaction volumes with the addition of 0.2 mg/mL bovine serum albumin (B8667, Sigma), 150 mM trehalose (T9531; Sigma) and 0.2% Tween 20 (28320; Pierce Thermo Fisher Scientific) and 5 μL template. Amplification reactions were performed in Cepheid SmartCycler II (Sunnyvale, Calif.). Each viral load was run in duplicates. As a negative control, HIV-1 negative plasma was used and processed in the same manner as the other samples.

Figure 17:
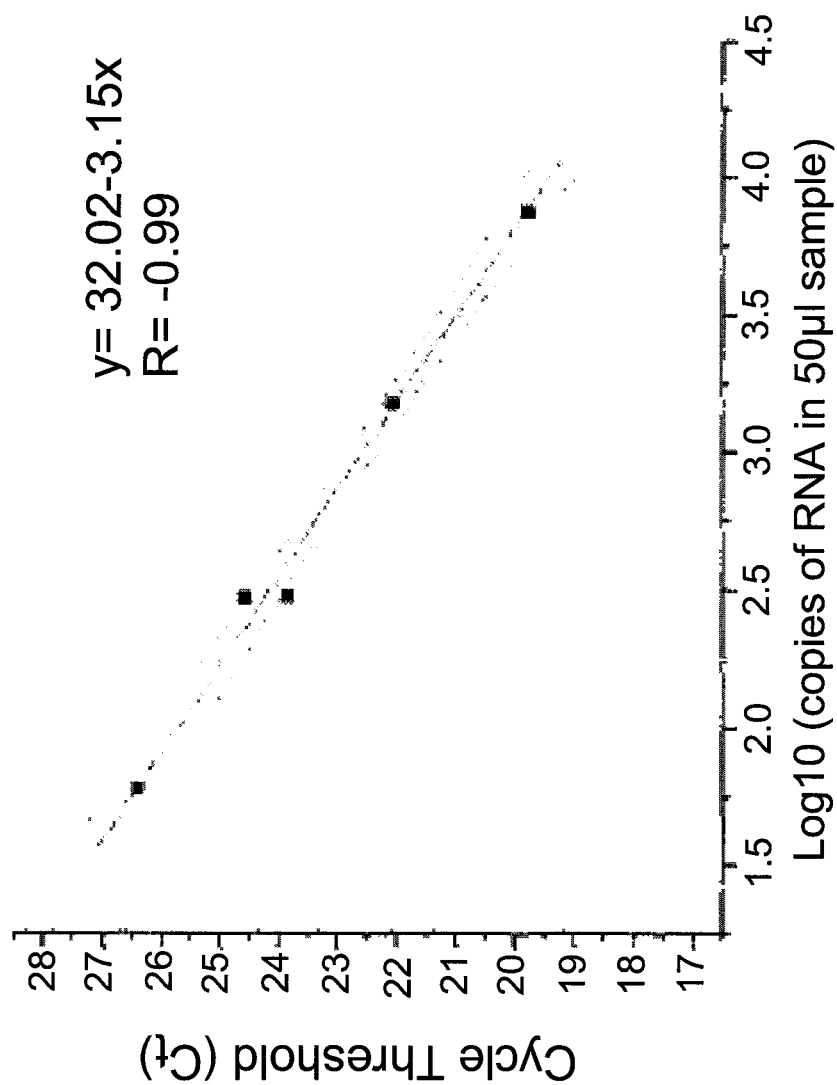
FIG. 17 shows quantitative RT-PCR for HIV-1 from plasma with Ambion PMPs stored in ACCUWIK membrane: standard curve of $C_T$ values for 4 different RNA concentrations plotted verses the $\log^{10}$ of the HIV-1 viral copy number. The solid squares are the $C_T$ values.
Figure 18:
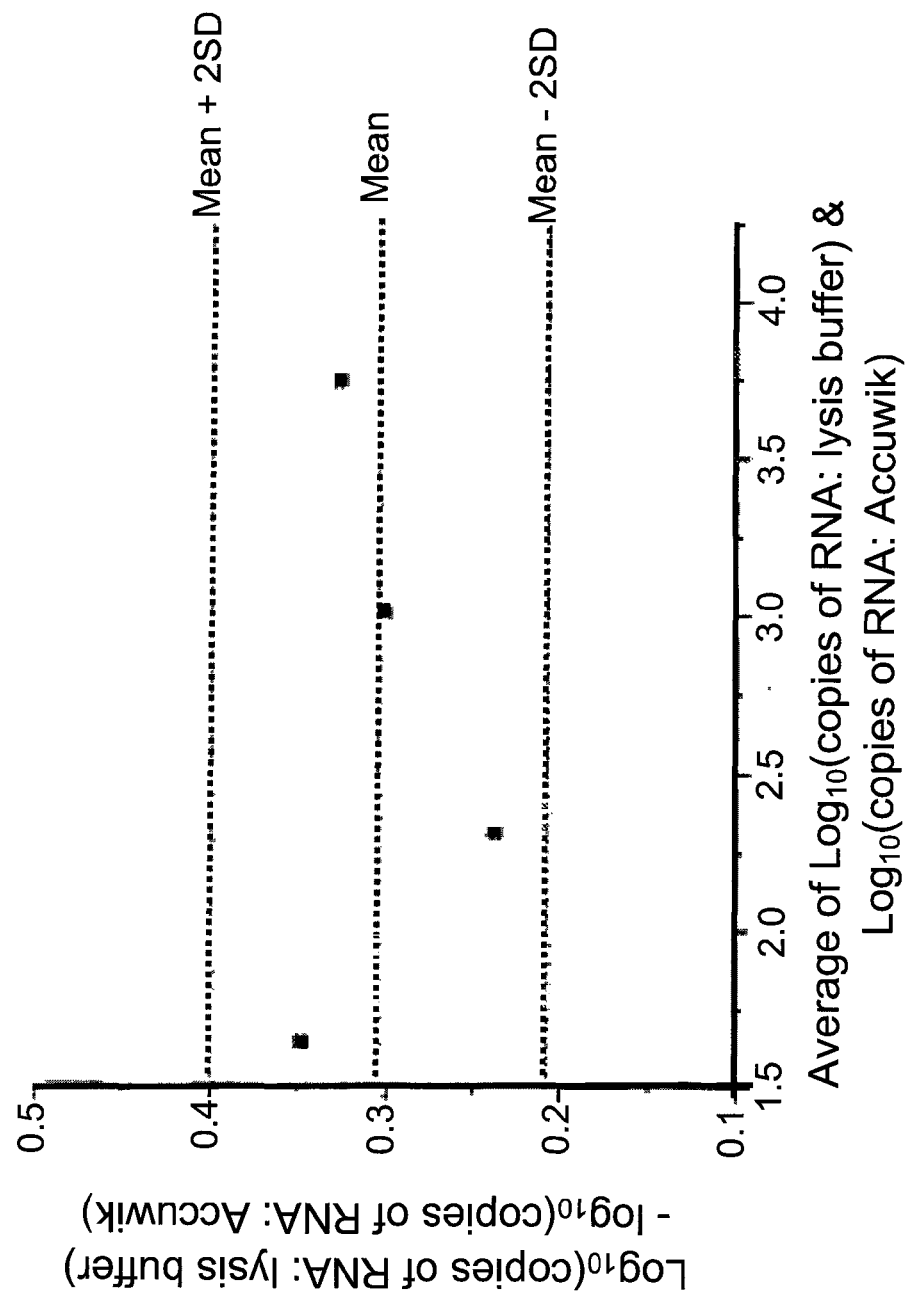
FIG. 18 shows a Bland-Altman plot comparing the samples with PMPs in lysis buffer and in ACCUWIK membrane: solid squares show difference between the two methods.

Viral RNA was purified from 50 μL of plasma spiked with HIV-1 virus. The purified RNA was amplified using the Abbott RealTime HIV-1 Amplification kit. A PCR efficiency of 107.7% was observed (SEE FIG. 17), indicating that the PMPs can be stored in the membrane without loss of RNA capture efficiency and be readily extracted for downstream processing. The loss of viral RNA in the filter membrane is minimal (SEE FIG. 18).

Example 11

Plasma Separation

The lateral flow system has been used in the detection and diagnosis of HIV. Current laboratory technologies rely on the combined and simultaneous detection of the HIV core (p24) protein and HIV-specific antibodies directed against HIV transmembrane proteins. Antibodies against these proteins consistently appear during seroconversion of HIV-infected individuals and remain throughout the course of infection. In the first 2 months after birth, HIV positive infants have increasing viral loads but are seropositive due to inheritance of maternal HIV antibodies, making existing tests ineffective. Moreover, HIV negative infants can be seropositive due to the same inheritance of maternal HIV antibodies. Detection of HIV in infants requires targeting the HIV core protein p24 as the principle marker for detection in order to verify their true infection state irrespective of the maternal sero-inheritance.

Experiments were performed during development of embodiments of the present invention to establish the utility of membrane-based blood separation for the purpose of metered plasma collection in a collection pad. Plasma separation devices were assembled using an 18 mm VIVID GF membrane and an 8 mm Ahlstrom 142 or 6 mm Pall A/D glass fiber collection pad. The collection pad was compressed 0.5 mm into the VIVID GF membrane. The VIVID membrane was sized to accommodate a fixed volume of blood, up to 125 μL, and the Ahlstrom/Pall membranes were sized to accommodate a fixed volume of 50 μL. The VIVID membrane was pre-treated with a solution containing 0.1% BSA protein, 0.5% sucrose and 0.1% Tween-20. 100 μL of pre-treatment solution was added to each VIVID membrane and left to air dry for 24 h at room temperature before being used. Fresh human blood samples of 100 μL or 125 μL in volume were added to the devices and the volume of plasma collection was calculated based on differences in mass of the collection membrane before and after blood separation.

For 125 μL of whole blood, 48±2 μL of plasma was collected with an average collection time of 8±2 min by both the Ahlstrom and Pall membranes. For 100 μL of whole blood, 37±2 μL of plasma was collected with an average collection time of 5±2 min also by both the Ahlstrom and Pall membranes. These data indicate that this membrane-based system can be used effectively for timed and metered collection of plasma from a whole blood sample.

Figure 19:
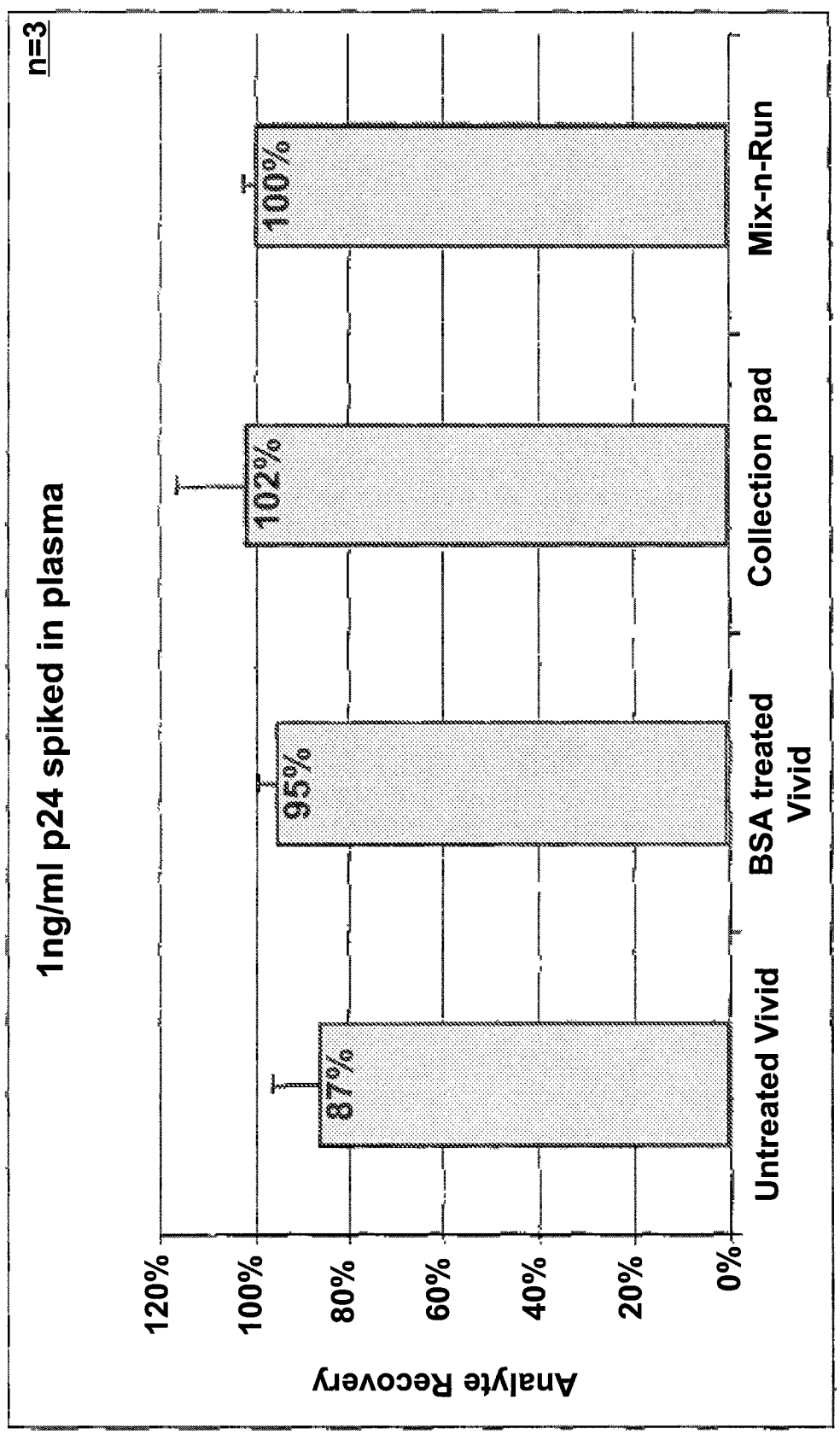
FIG. 19 shows blood separation and plasma collection membranes do not significantly bind p24 protein analyte.

Experiments were conducted during development of embodiments of the present invention to determine the extent of non-specific analyte losses to the VIVID membrane and the Ahlstrom collection pad, wherein the HIV protein antigen p24 was diluted in human plasma and passed through separation devices. Separation devices were assembled as described above. For one separation device, the VIVID membrane was not pre-treated with BSA/Sucrose/Tween. In a second, the 0.1% BSA protein, 0.5% sucrose and 0.1% Tween-20 solution was applied as a pre-treatment as described above. A third sample was prepared with 50 μL of plasma containing 1 ng/mL p24 analyte added directly to the Ahlstrom collection pad. Lastly, 50 μL of plasma containing p24 analyte was added directly to a tube containing assay buffer and this reference reaction was labeled mix and run. Each reaction tube was pulse vortexed to mix the reaction thoroughly. Each tube was then placed in the heat block at 95° C. for 4 min. Each tube was then allowed to cool at room temp (23° C.) for 4 min. Biotinylated monoclonal antibody against one epitope of p24 was added to each reaction vessel. After 1 min, 13.5 µL of carbon conjugate coated with a monoclonal antibody against a second epitope of p24 was added to the reaction. After brief mixing, a test strip containing a neutravidin test line and an anti-mouse control line was added to the reaction. Test strips were quantified using a camera after being dried through background subtraction of the test line signal. Only marginal recovery losses (e.g., non-specific binding) of p24 were observed in the separation device fitted with an untreated VIVID membrane (SEE FIG. 19). For all the other samples, an equivalent output as to the reference mix and run reaction was obtained, indicating no significant loss of the analyte signal to either the VIVID membrane or the Ahlstrom collection pad.

Example 12

Plasma Separation and p24 Detection

Figure 20:
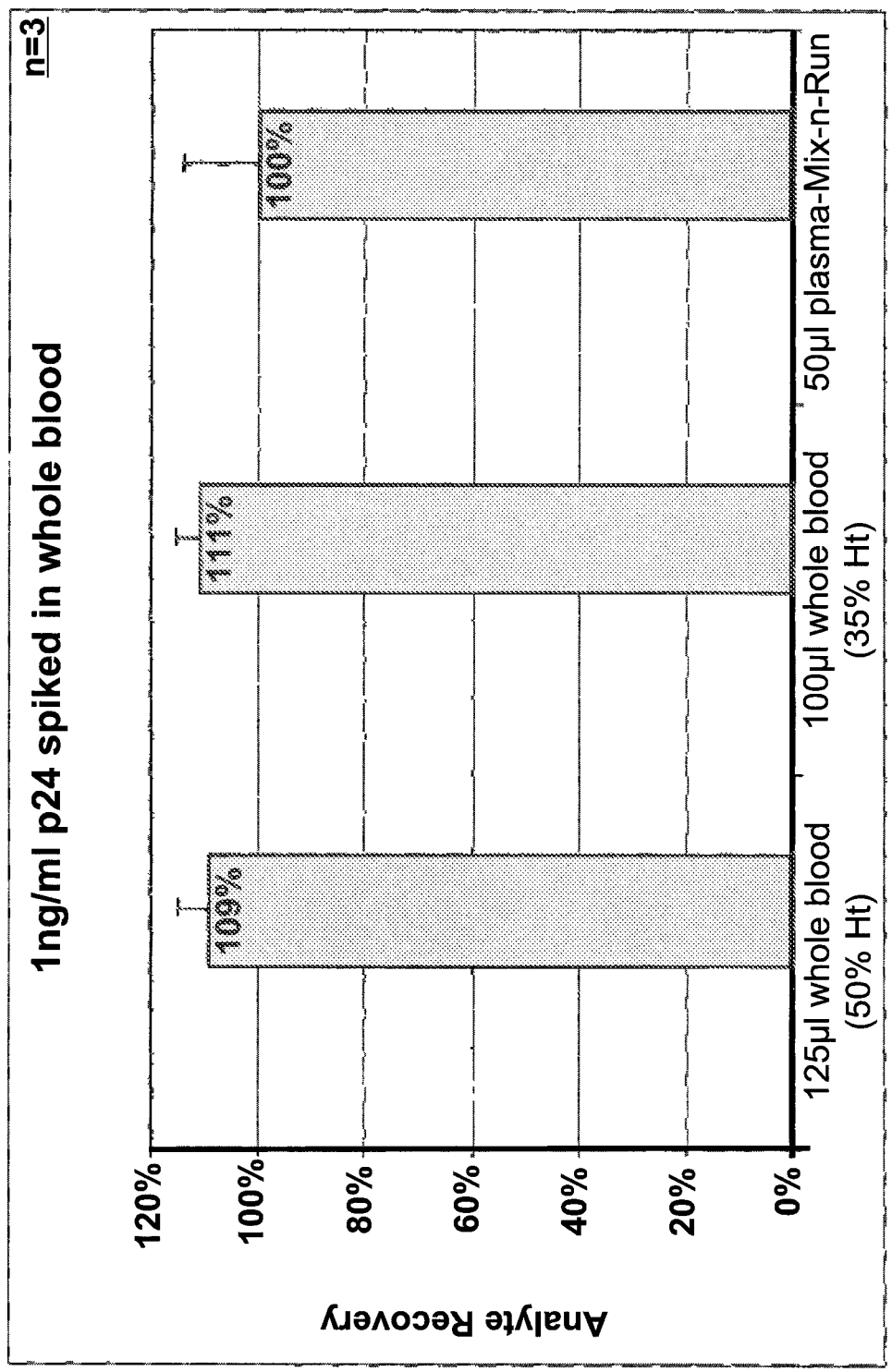
FIG. 20 shows no loss of analyte-specific signal is observed in plasma collected from analyte-spiked whole blood separated with a device of the present invention.

Experiments were performed during development of embodiments of the present invention to assess the recovery of the p24 analyte spiked into whole blood and recovered from plasma after separation. Blood samples were reconstituted from a fresh blood sample with two hematocrit (Ht) values (50% and 35% Ht) that reflect the clinical range found in human specimen. Volumes from each sample were used (125 µL from the 50% Ht and 100 µL from the 35% Ht) so that the total available plasma volume for recovery was the same (60 µL, of which a maximum of 50 µL can be absorbed by the collection membrane). Separation devices were assembled and reconstituted whole blood (125 µL from the 50% Ht and 100 µL from the 35% Ht) were applied to the separation devices and plasma collected from the pad of each of these was subjected to the assay for signal readout. An additional reference reaction was performed whereby 50 µL of plasma containing the 1 ng/mL p24 analyte was added directly to the assay buffer and labeled mix and run. The amount of analyte recovered from applying both the 35% and 50% Ht blood samples is comparable to the mix and run reference reaction (SEE FIG. 20), indicating that this plasma separation device can be used to successfully recover protein analyte from whole blood samples with no detectable loss of analyte incurred through the separation of the cellular blood phase.

Figure 21:
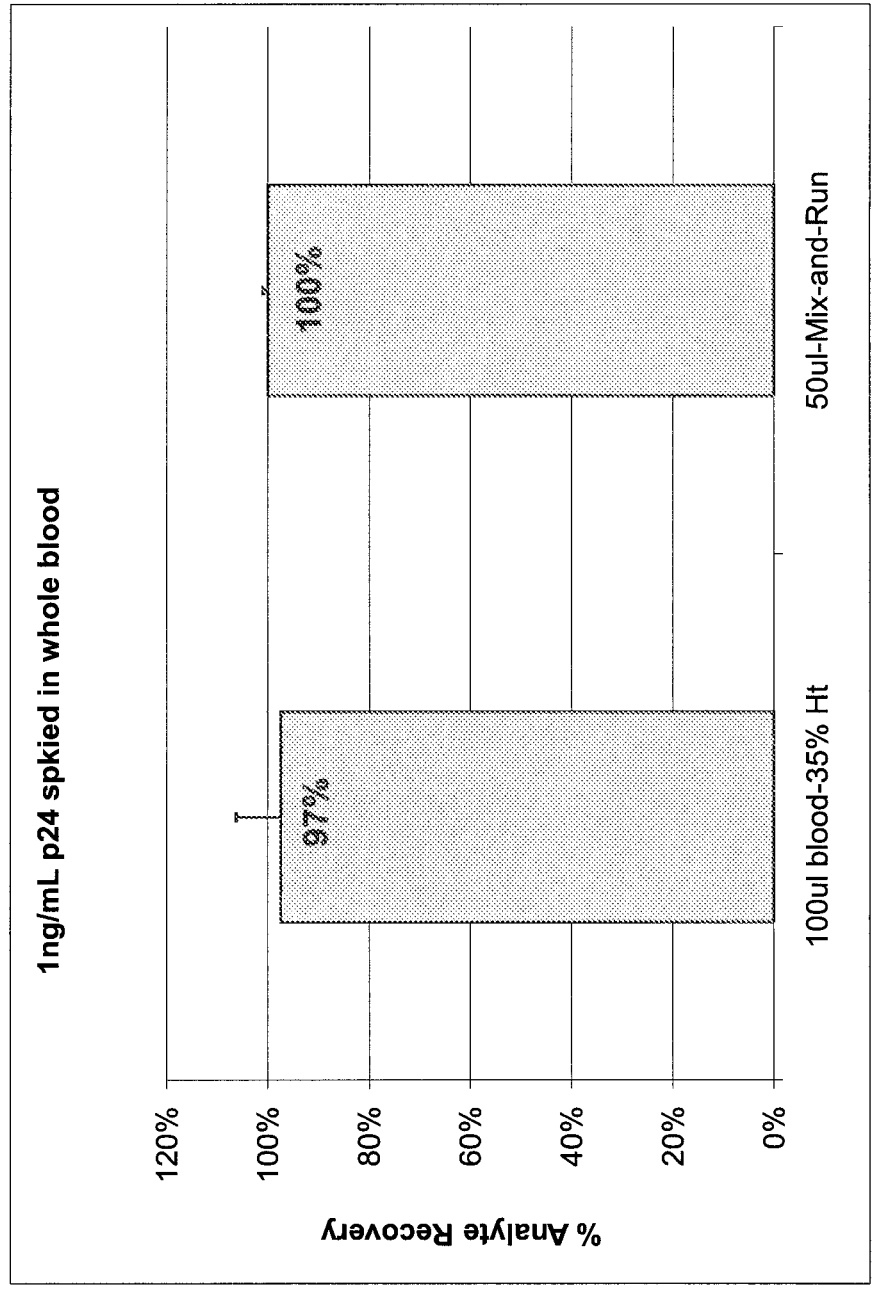
FIG. 21 shows no loss of analyte-specific signal is observed in plasma collected from analyte-spiked whole blood separated with a device of the present invention.

The same experiment was performed by assembling separation devices fitted with Pall A/D membrane in place of Ahlstrom 142 and reconstituting whole blood at 35% Ht spiked in with 1 ng/mL of p24 analyte. As before, an additional reference reaction was performed whereby 50 µL of plasma containing the 1 ng/mL p24 analyte was added directly to the assay buffer and labeled mix and run. The amount of analyte recovered from applying the 35% Ht blood samples containing p24 is comparable to the mix and run reference reaction (SEE FIG. 21). This result confirms that the ability to collect and elute p24 analyte into a membrane is applicable different compositions of collection membrane.

Example 13

Assay Reagent Storage in Plasma Separation Module

Figure 22:
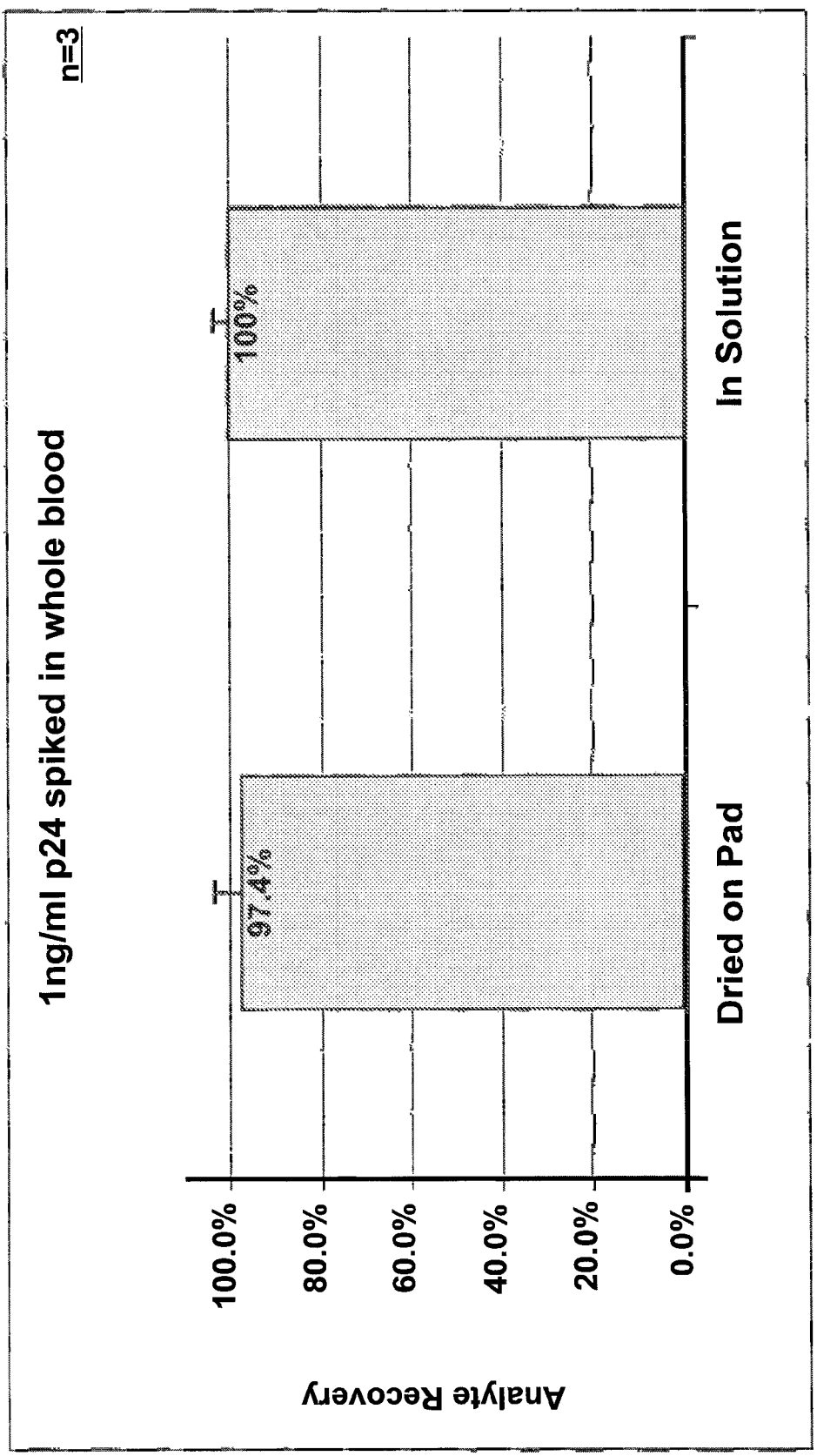
FIG. 22 shows that signal output of collection pads dried down with assay-specific detergents is comparable to reactions with detergents in solution.

Experiments were performed during development of embodiments of the present invention to demonstrate the feasibility of storing assay reagents into the plasma collecting membrane. In some embodiments, the lateral flow assay utilizes a specific concentration of detergents, namely SDS and NP-40, in order to allow for viral (HIV) disruption and analyte (p24 protein) release from HIV infected samples. Thus for a 50 µL plasma sample, 100 µL of PBS buffer containing 0.2% SDS and 0.67% NP-40 is optimally required for virion disruption and p24 recovery. Experiments were performed where 10 µL of a ten-fold concentrated stock of detergent solution (2.0% SDS and 6.7% NP-40) was applied to a collection pad and allowed to dry for 24 h at room temperature. It was then assembled into a separation device and plasma collected from a 100 µL whole blood sample spiked in with 1 ng/mL of the p24 analyte. Output was measured against a solution-phase mix and run reference reaction with an equivalent volume (50 µL) of plasma. The assay output from the detergent dried down in the pad was comparable to solution-phase mix and run reference reaction, indicating that the dry down of the assay reagents is feasible and compatible in the collection pad membrane (SEE FIG. 22).

Example 14

In-Pad Dry-Down of Detergents and Analyte

Evaluations were performed whereby 10 µL of a ten-fold concentrated stock of detergent solution (2.0% SDS and 6.7% NP-40) was applied to a collection pad and allowed to dry for 24 h at room temperature. Then 50 µL of plasma with or without 1 ng/mL of the p24 analyte was added to the pad and allowed to dry for 24 h at room temperature. The samples were then reconstituted with 125 µL of PBS buffer, mixed by flicking the tube containing the pad and buffer and analyzed. The assay output from the detergent/p24 dried down in the pad was comparable to solution-phase mix and run reference reaction, indicating that the dry down of the assay reagents as well as p24 protein used as a potential reference standard (positive and negative controls) for an assay is feasible and compatible in the collection pad membrane (SEE FIG. 23).

Example 15

Device with Clam-Shell Type Filter Module

Figure 23:
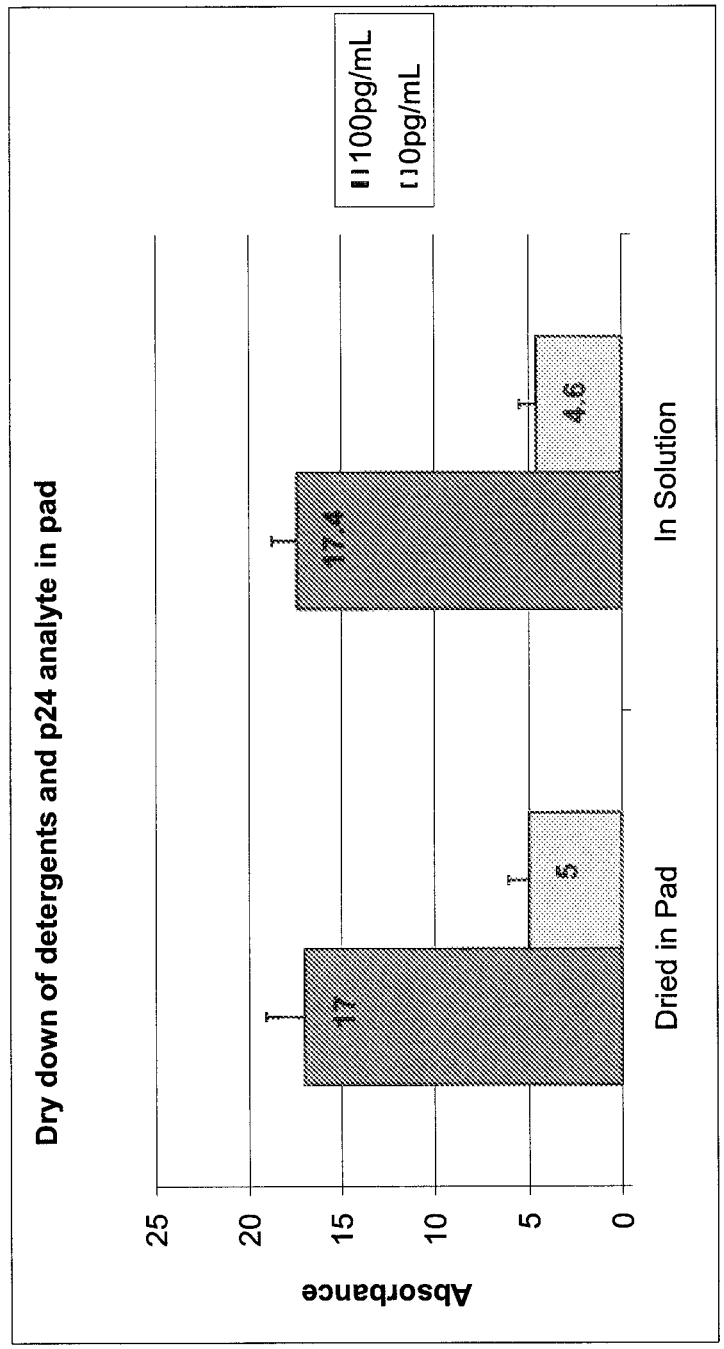
FIG. 23 shows that signal output of collection pads dried down with assay-specific detergents and protein analyte is comparable to reactions with detergents and analyte in solution.
Figure 30:
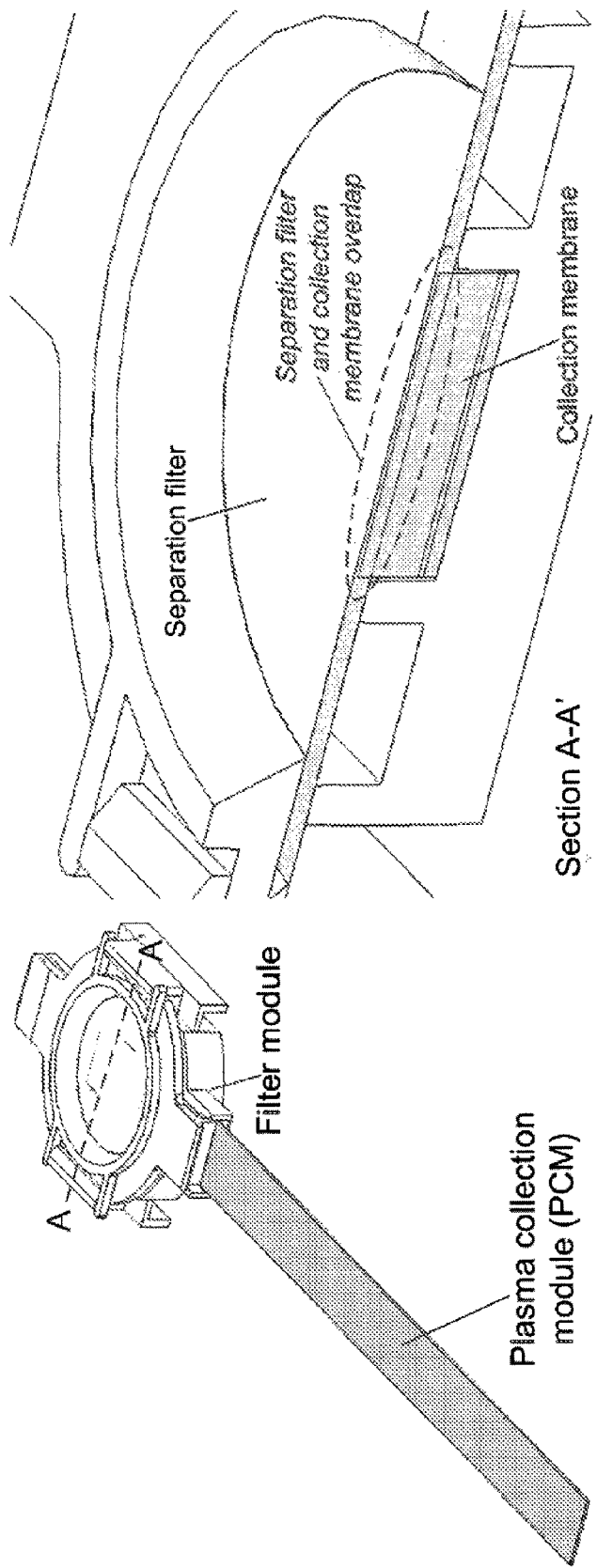
FIG. 30 shows (left) a schematic of the collection element integrated with the filter element, where the top-half of the clam shell has been folded down and locked via the locking tabs; (right) this allows the separation filter and collection membrane to overlap and compress together, which facilitates the blood separation.
Figure 31:
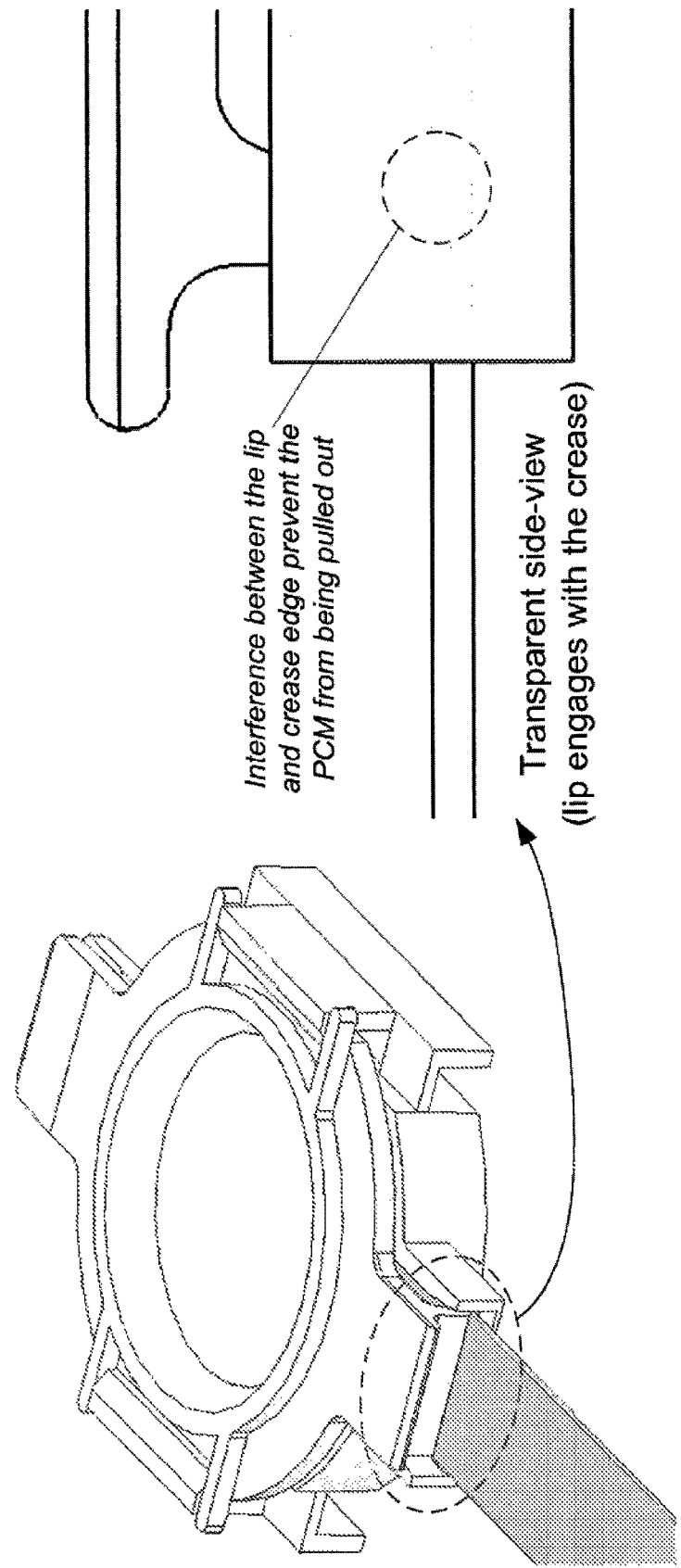
FIG. 31 shows (left) a schematic showing the assembled module for blood separation; and (right) a transparent side-view of the assembled module showing the lip engaging with the crease in the collection element substrate test strip.

In some embodiments, the present invention provides a filter module with a clam shell design (SEE FIG. 24) which is closed by folding and latching the top-half via locking tabs (SEE FIG. 23). In some embodiments, a clam-shell type filter module comprises a slot for a collection test strip designed to accept the width of the collection test strip. In some embodiments, the entrance to the slot has both chamfered edges and a filleted bottom edge to assist in guiding a collection module into the clam shell without interference. In some embodiments, the depth of the slot is designed such that there is an overlap between the collection membrane and separation filter (SEE FIG. 30). In some embodiments, a clam-shell type filter module comprises locking tabs (e.g., two (left and right) locking tabs) that allow for latching the top-half closed (SEE FIG. 25). In some embodiments, the clam shell is opened by an operator by squeezing on the bottom half of the locking tabs to pivot it open and release the top-half of the clam shell. In some embodiments, a living hinge is integrated into the clam shell design. In some embodiments, the plastic component of the clam shell is made from polypropylene. In some embodiments, the living hinge provides the capacity to open and close the clam shell thousands of times, although the actual process only requires it to flex a few times. In some embodiments, a clam-shell type filter module comprises one or more pockets (e.g. 1, 2, 3, 4, 5, 6, 7, 8, 9, 10, . . . 20). In some embodiments, the pockets serve to keep uniform thickness of the molded part, which prevents warping and sink marks, e.g., due to uneven cooling. In some embodiments, the wall thickness for the pockets is uniform. In some embodiments, a clam-shell type filter module comprises a lip. In some embodiments, when the top-half of the clam shell is locked using the locking tabs, the lip engages with a crease in the collection modules (SEE FIG. 31). Once engaged and locked into place, the collection test strip cannot fall out of the clam shell on its own until the operator releases the top-half of the clam shell. In some embodiments, a clam-shell type filter module comprises latch guards (e.g., 4 latch guards). In some embodiments, latch guards prevent the top-half of the clam shell from sliding back and forth once it has been locked into place via the locking tabs. In some embodiments, the latch guards engage with the edges of the locking tabs (SEE FIG. 25). In some embodiments, a clam-shell type filter module comprises an energy director. In some embodiments, an energy director facilitates bonding of the separation filter to the clam shell via ultrasonic welding (SEE FIGS. 26-27). In some embodiments, the triangular energy director is designed such that its height is approximately the same as the thickness of the separation filter. In some embodiments, ultrasonic welding creates a pseudo ring barrier since the energy director plastic melts and flows into the separation filter. The pseudo ring barrier facilitates higher performing separations. In some embodiments, the membrane is bonded using heat sealing, laser welding, adhesives, etc. In some embodiments, a clam-shell type filter module comprises a back wall. In some embodiments, the back wall of the slot serves as a stopping point for positioning the collection modules. When the collection module is positioned to make contact with the back wall, the crease automatically aligns with the lip of the clam shell (SEE FIG. 31).

In some embodiments, a clam-shell type filter module is configured to connect to, function with, and/or integrate with a separation filter. In some embodiments, a clam-shell type filter module is integrated with a separation filter (e.g., Pall Vivid) (SEE FIG. 26). In some embodiments, the separation filter is any suitable filter, as described herein and elsewhere. In some embodiments, the separation filter is bonded to the top-half of the clam shell via ultrasonic welding using the energy director. In other embodiments, the separation filter is bonded using heat sealing, laser welding, adhesives, etc. In some embodiments, when the separation filter is bonded to the top-half of the clam shell and closed, the separation filter is essentially flush with the bottom-half of the clam shell (SEE FIG. 27, right). In some embodiments, ultrasonic welding provides the ability for the molded plastic of the energy director to melt, flow, and fuse into the separation filter, creating a pseudo ring barrier which further facilitates the separation by limiting excess void volume inside the separation filter which reduces the amount of plasma captured by the collection membrane.

In some embodiments, a clam-shell type filter module is configured to connect to, function with, and/or integrate with a collection module (e.g., plasma collection module, plasma collection module, etc.). In some embodiments, a collection module comprises a collection membrane (e.g., Pall A/D). In some embodiments, the collection membrane is the component which collects and absorbs the specimen of interest, e.g., plasma. In some embodiments, a collection module comprises three primary components—substrate test strip, adhesive, and collection membrane. In some embodiments, the substrate test strip is a thin plastic sheet that is flexible enough to be creased and perforated, but also sufficiently stiff to hold the adhesive and collection membrane. In some embodiments, the collection module is manufactured using standard technology currently utilized for similar lateral flow test strips. In some embodiments, the crease in the test strip serves to align and mate with the lip of the clam shell (SEE FIG. 31). In some embodiments, proper orientation of the crease ensures that the lip engages with the sharp right-angle to prevent the strip from falling out of the clam shell. In some embodiments, the strip is also perforated to allow the operator to easily pull on the collection module, and to tear it into two separate pieces, if desired for the assay procedure. In some embodiments, a diagnostic compatible double-sided adhesive (3M, St Paul, Minn.) is used to bond the collection membrane to the substrate test strip. In some embodiments, the adhesive is diagnostic compatible (i.e., does not contain or release any bio-chemical inhibitors that would interfere with the bio-chemical assay) and double-sided to bond securely to both material types (substrate test strip and collection membrane). In some embodiments, the adhesive withstands limited exposures to elevated temperatures (<100° C.) and liquids (plasma, buffered salt solutions with concentrations ≤150 mM, and detergents, such as SDS and NP-40, with concentrations ≤0.15% and 0.5%, respectively). In some embodiments, the collection membrane (e.g., Pall A/D) is sized to be the same as the width of the collection strip, and matches the geometry of the adhesive in the other axis.

Figure 29:
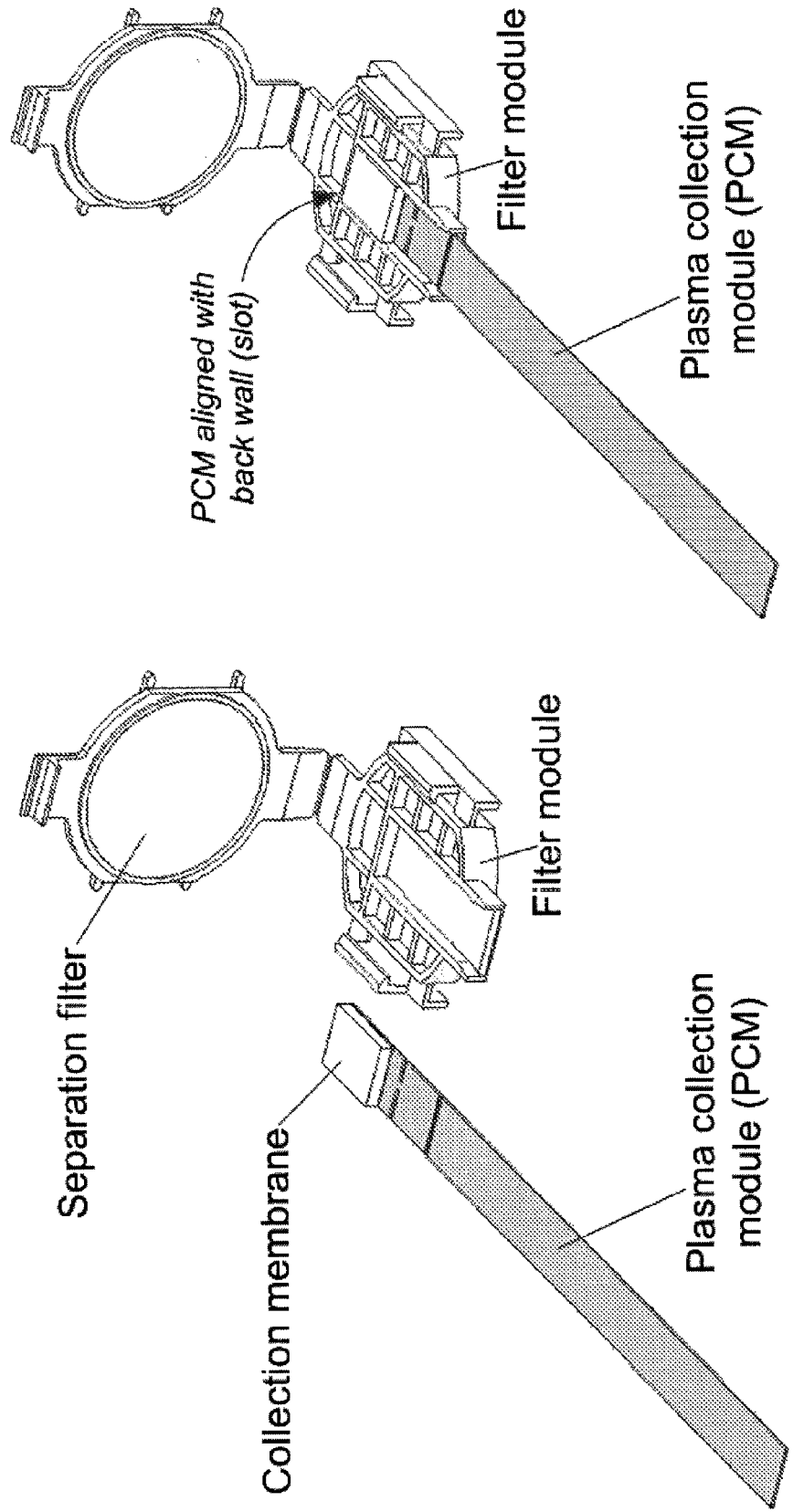
FIG. 29 shows (left) schematics of both the plasma collection element and filter element with their respective membrane and filter; and (right) the collection element slid into the filter element via the slot and aligned with the back wall.

In some embodiments, to separate the blood sample, the plasma collection module (PCM) is inserted into the filter module (SEE FIG. 29). With the filter module in the open position, the PCM is slid down the slot and aligned with the back wall, ensuring that the collection membrane is concentric with the separation filter and that the lip will align with the crease on the PCM's substrate test strip.

In some embodiments, the height of the slot in the filter module is designed such that there is an overlap between the separation filter and collection membrane. In some embodiments, the overlap facilitates compression between the separation filter and collection membrane. In some embodiments, compression facilitates blood separation (SEE FIG. 30).

Figure 28:
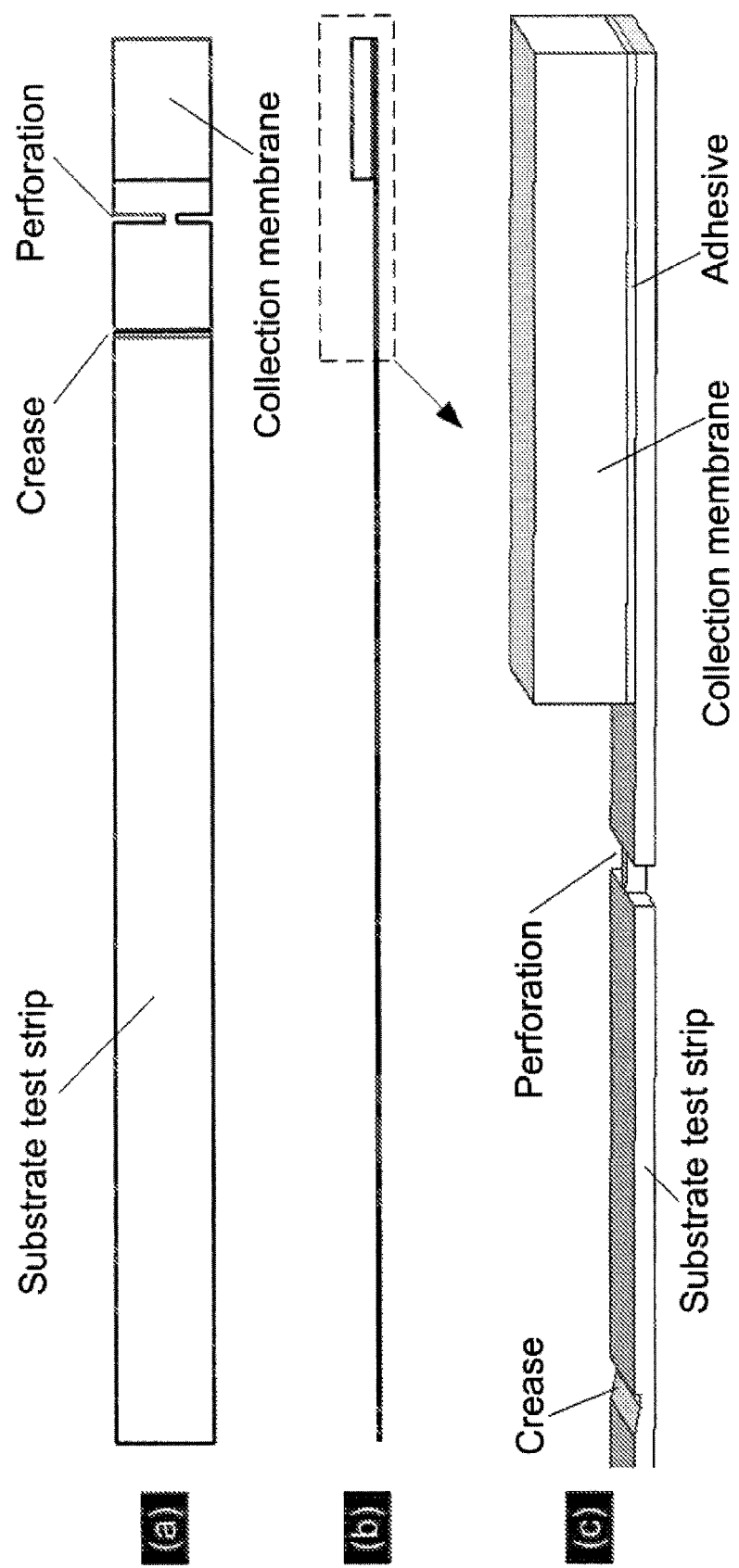
FIG. 28 shows (a) top-view schematic of the plasma collection element, a plastic substrate test strip holds a small piece of double-sided diagnostic compatible adhesive, which bonds the collection membrane to the substrate test strip; (b) side view of the collection element; (c) exploded view of the side-view (red dashed box) showing the crease, perforation, and thin adhesive layer bonding the substrate test strip and collection membrane.

In some embodiments, when the PCM is inserted into the filter module, and the clam shell is closed, the lip of the clam shell (SEE FIG. 24) engages with the crease in the substrate test strip (SEE FIG. 28). In some embodiments, the lip slightly compresses into the PCM, ensuring that it is holding firmly onto the PCM. In some embodiments, the back edge of the lip engages with the edge of the crease (SEE FIG. 31), which prevents the PCM from slipping out of the clam shell.

Figure 32:
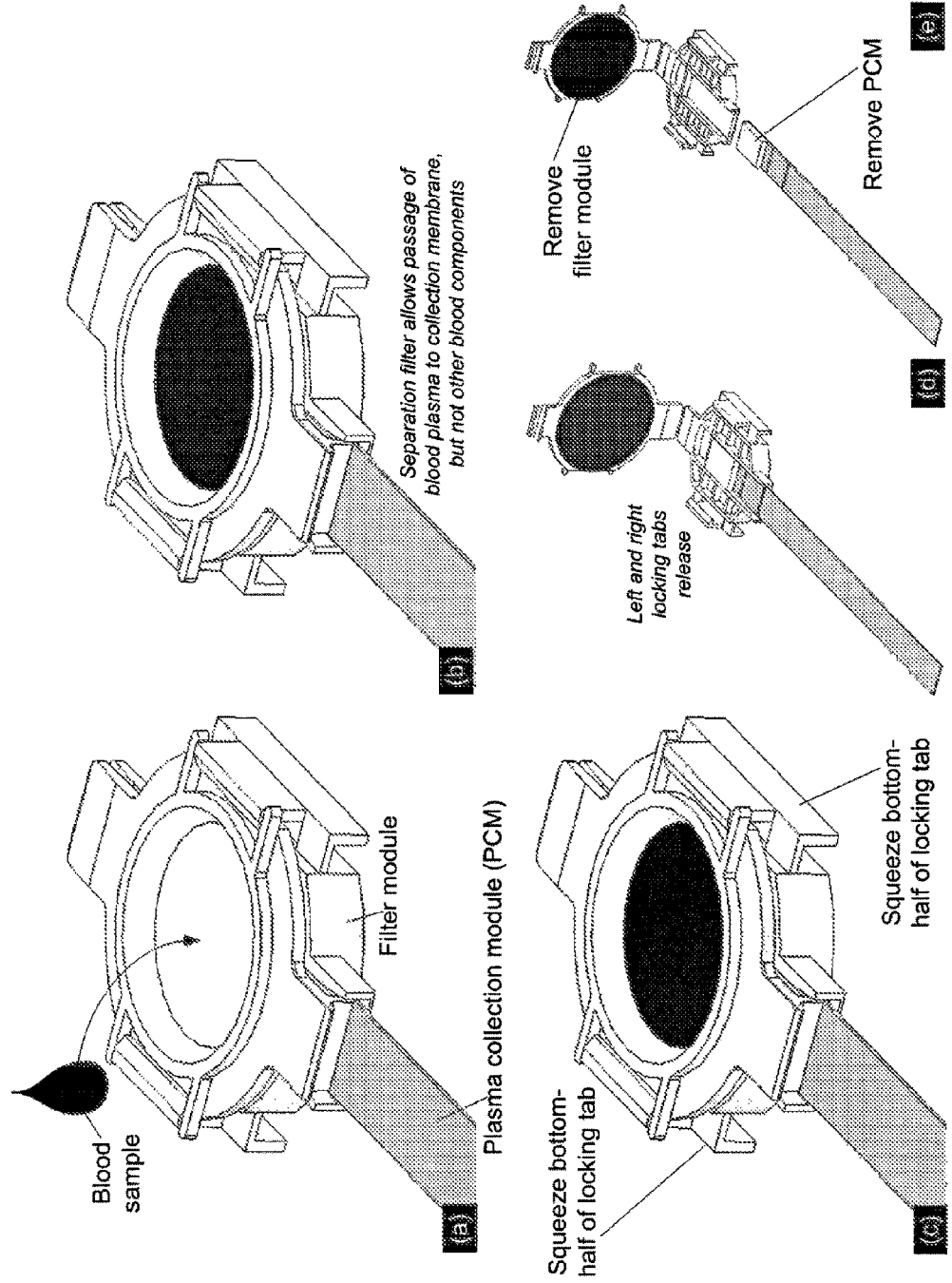
FIG. 32 shows a step-by-step overview of the blood separation process using a clam-shell filter element and plasma collection element: (a) dispense blood sample onto separation filter; (b) the separation filter passes the plasma through to the collection membrane; (c-d) the operator squeezes the bottom-half of the left and right locking tabs to unlatch the top-half of the filter element; and (d) the filter element and collection element are separated from one another and may be used for subsequent test processes (e.g., CD4 count, PCR, immunoassay)

This embodiment of the present invention is used to perform a blood sample separation (SEE FIG. 32). The operator dispenses the prescribed volume of blood onto the separation filter. After waiting a few minutes, the separation filter allows passage of the blood plasma, but no other blood components, to the collection membrane on the collection module. Intimate contact between the separation filter and collection membrane allows passage of blood plasma and facilitates blood separation (SEE FIG. 30). Once the separation has finished, the operator squeezes the bottom-half of the left and right locking tabs to pivot the tabs outward and release the top-half of the filter module. At this stage, the crease of the collection is no longer engaged with the lip and the collection module can be removed by the user. The collection module is removed from the filter module. Either or both modules may be used for subsequent test processes.

In some embodiments, the patient's CD4 count may be monitored using the filter module which contains the cellular blood components. In some instances, the collection module, which contains the blood plasma component, may be used for measuring viral load using PCR or related biochemical reaction. For example, PMPs either separate from or embedded into the PCM may be used for viral RNA extraction from the blood plasma and elute them directly into the buffer for PCR related processing. In some instances, the PCM may be used in a lateral flow system for the detection of HIV antibodies, p24 protein, etc. In some instances, the filter module and/or PCM may be transported to a secondary clinic for any of the aforementioned biochemical processes.

REFERENCES

All publications and patents mentioned in the above specification and/or listed below are herein incorporated by reference. Various modifications and variations of the described compositions and methods of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the present invention. The following references are incorporated by reference in their entireties:

Kelso D, Sur K, Parpia Z: Barriers for facilitating biological reactions. U.S. Pat. App. No. 20090246782, Oct. 1, 2009.
Brenner T, Haeberle S, Zengerle R, Ducree J: Continuous centrifugal separation of whole blood on a disk. SPECIAL PUBLICATION-ROYAL SOCIETY OF CHEMISTRY 2004, 296:566568.
Haeberle S, Brenner T, Zengerle R, Ducree J: Centrifugal extraction of plasma from whole blood on a rotating disk. Lab on a Chip 2006, 6:776-781.
Kang J, Cho H, Kwak S, Yoon D, Kim T: Novel particle separation using spiral channel and centrifugal force for plasma preparation from whole blood. SPECIAL PUBLICATION-ROYAL SOCIETY OF CHEMISTRY 2004, 296:614-616.
Madou M, Lee L, Daunert S, Lai S, Shih C: Design and fabrication of CD-like microfluidic platforms for diagnostics: microfluidic functions. Biomedical Microdevices 2001, 3:245-254.
Toner M, Irimia D: Blood-on-a-chip. Annual Review of Biomedical Engineering 2005, 7:77-103.
Luo W, Yang H, Rathbun K, Pau Cop, Ou CoY: Detection of Human Immunodeficiency Virus Type 1 DNA in Dried Blood Spots by a Duplex Real-Time PCR Assay. J Clin Microbio/2005, 43:1851-1857.
Blattert C, Jurischka R, Tahhan I, Schoth A, Kerth P, Menz W: Separation of blood in microchannel bends. In.; 2004
Kondo A, Kitajima M: MUltilayered integral chemical analysis element for the blood. Fuji Photo Film Co., Ltd., 1981.
Vogel P, Braun H, Berger D, Werner W: Process and composition for separating plasma or serum from whole blood. (USPTO ed.: Boehringer Mannheim GmbH; 1984.
Vogel P, Braun H, Berger D, Werner W: Device for separating plasma or serum from whole blood and analyzing the same. Boehringer Mannheim GmbH; 1989.
Baumgardner J, Loewen M: Blood separation media and method for separating plasma from whole blood. Ahlstrom Filtration, Inc.; 1993.
Loewen M D, Baumgardner J S: Development of a nonwoven filler for separation of serum from whole blood for medical diagnostic applications. Tappi Journal 1996, 79:183-184.
Simon L D: Blood separation medium useful for separating erythrocytes from whole blood comprises non-woven web of fibrillated and non-fibrillated synthetic staple fibers. pp. 6: SIMON L D (SIMO-Individual) AHLSTROM MT HOLLY SPRINGS LLC (AHLS Non-standard):6.
Hillman R, Gibbons I: Blood separation device comprising a filter and a capillary flow pathway eXiting the filter. Biotrack, Inc.; 1988.
Suzuki H, Ho C M: A magnetic force driven chaotic micromixer. pp. 40-43; 2002:40-43.
Chien S: Red cell deformability and its relevance to blood flow. Annual Review of Physiology 1987, 49:177-192.
Baskurt O K, Meiselman H J: Blood rheology and hemodynamics. Seminars in Thrombosis and Hemostasis 2003, 29:435-450.
Benson K: MCAT review. Emory University 1999:141-199.
Huang S, Salituro J, Tang N, Luk K-C, Hackett Jr. J, Swanson P, Cloherty G, Mak W-B, Robinson J, Abravaya K: Thermodynamically modulated partially double-stranded linear DNA probe design for homogeneous real-time PCR. Nuc Acids Res 2007, 35:e101.
Mylonakis E, Paliou M, Rich J: Plasma viral load testing in the management of HIV infection. Am Fam Physician 2001, 63:483-490.
Dineva M A, Mahilum-Tapay L, Lee H: Sample preparation: a challenge in the development of point-of-care nucleic acid-based assays for resource-limited settings. Analyst 2007, 132:1193-1199.

We claim:

1. A method of filtering blood plasma, comprising:
providing a device comprising a plasma separation membrane configured to allow passage of blood plasma more rapidly than cellular blood components and a plasma collection pad configured to draw blood plasma into the plasma collection pad by capillary action, wherein the plasma collection pad accommodates a fixed volume of plasma;
with the plasma collection pad in direct contact with the plasma separation membrane, applying a blood sample to the plasma separation membrane, wherein blood plasma is collected in the plasma collection pad;
wherein the fixed volume of plasma of the plasma collection pad is greater than the volume of plasma collected in the plasma collection pad;
separating the plasma collection pad from the plasma separation membrane; and
inserting the plasma collection pad into a tube for analysis.

2. The method of claim 1, further comprising drawing blood plasma through the plasma separation membrane, wherein said drawing is passive.

3. The method of claim 2, wherein said drawing does not require electrophoresis, centrifugation, or greater than atmospheric pressure.

4. The method of claim 1, wherein said plasma separation membrane accommodates a fixed volume of blood sample.

5. The method of claim 1, wherein said fixed volume of said plasma collection pad is smaller than a volume of said plasma separation membrane.

6. The method of claim 1, wherein said fixed volume of said plasma collection pad is independent of the volume of blood sample applied to the membrane.

7. The method of claim 1, wherein said fixed volume of said plasma collection pad is independent of the hematocrit of said blood sample.

8. The method of claim 1, further comprising:

storing said plasma in said plasma collection pad.

9. A device for separating plasma from whole blood, comprising:

a filter module comprising (i) a plasma separation membrane configured to allow passage of blood plasma but not other blood components, and (ii) a collection module comprising a plasma collection pad and a tube, wherein the filter module and the collection module are attached such that the plasma separation membrane and plasma collection pad are in intimate contact to draw blood plasma from the plasma separation membrane by capillary action; and wherein the plasma collection pad is separable from the plasma separation membrane and the plasma collection pad is insertable into the tube; wherein the plasma collection pad accommodates a fixed volume of plasma that is greater than a volume of plasma drawn into the plasma collection pad.

10. The device of claim 9, wherein said plasma separation membrane accommodates a fixed volume of whole blood.

11. The device of claim 9, wherein said fixed volume of said plasma collection pad is smaller than a volume of said plasma separation membrane.

12. The device of claim 9, wherein said plasma separation membrane comprises an asymmetric polysulfone membrane.

13. The device of claim 9 wherein said plasma collection pad comprises glass fiber.

14. The device of claim 9, comprising paramagnetic particles in said plasma collection pad.

15. The device of claim 9, comprising assay reagents in said plasma collection pad.

16. The method of claim 1, wherein said analysis comprises detecting a p24 protein in the separated plasma.

17. The method of claim 1, wherein said analysis comprises a lateral flow system for detecting one or more of HIV antibodies and p24 protein.

* * * * *